(12) United States Patent
Banowski et al.

(10) Patent No.: US 8,354,096 B2
(45) Date of Patent: Jan. 15, 2013

(54) WATER-FREE ANTIPERSPIRANT SPRAYS WITH IMPROVED SUBSTANCE

(75) Inventors: Bernhard Banowski, Dusseldorf (DE); Nadine Buse, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/245,082

(22) Filed: Sep. 26, 2011

(65) Prior Publication Data

US 2012/0014897 A1    Jan. 19, 2012

Related U.S. Application Data

(63) Continuation of application No. PCT/EP2010/054099, filed on Mar. 29, 2010.

(30) Foreign Application Priority Data

Apr. 1, 2009  (DE) .......................... 10 2009 002 098

(51) Int. Cl.
*A61Q 15/00* (2006.01)
*A61K 8/18* (2006.01)

(52) U.S. Cl. .......................................... 424/65; 424/401

(58) Field of Classification Search .................. None
See application file for complete search history.

(56) References Cited

U.S. PATENT DOCUMENTS

| 2,571,030 A | 10/1951 | Govett et al. |
| 3,833,721 A | 9/1974 | Saute et al. |
| 3,887,692 A | 6/1975 | Gilman |
| 3,904,741 A | 9/1975 | Jones et al. |
| 4,359,456 A | 11/1982 | Gosling et al. |
| 4,775,528 A | 10/1988 | Callaghan et al. |
| 5,976,514 A * | 11/1999 | Guskey et al. ............... 424/65 |
| 6,010,688 A | 1/2000 | Shen |
| 6,042,816 A | 3/2000 | Shen |
| 6,074,632 A | 6/2000 | Shen |
| 6,245,325 B1 | 6/2001 | Shen |
| 6,663,854 B1 | 12/2003 | Shen et al. |
| 6,902,723 B2 | 6/2005 | Shen |
| 2004/0009133 A1 | 1/2004 | Kolodzik et al. |
| 2006/0079414 A1* | 4/2006 | Nieendick et al. ............ 510/119 |
| 2007/0077221 A1* | 4/2007 | Seigneurin et al. ......... 424/70.16 |

FOREIGN PATENT DOCUMENTS

| EP | 0006232 A1 | 1/1980 |
| EP | 0006234 A1 | 1/1980 |
| FR | 2859907 A1 | 1/2006 |
| GB | 1347950 A | 2/1974 |
| GB | 2048229 A | 12/1980 |

OTHER PUBLICATIONS

PCT International Search Report (PCT/EP2010/054099) dated Sep. 26, 2011.

* cited by examiner

*Primary Examiner* — Frederick Krass
*Assistant Examiner* — Michael Cohen
(74) *Attorney, Agent, or Firm* — David K. Benson

(57) ABSTRACT

An antiperspirant composition for personal hygiene is formulated as a suspension which can be sprayed with or without a propellant, and contains at least one antiperspirant substance, 0-5 wt. % free water, based on the weight of the propellant-free composition, and triethylcitrate and at least one additional cosmetic oil, which is liquid under normal conditions, as a carrier. The weight fraction of the triethylcitrate with respect to the total amount of oils is between 13-50 wt. % based on the total weight of the propellant-free composition. The composition also includes and 0 to less than 1 wt. % cyclomethicone, based on the weight of the propellant-free composition.

16 Claims, No Drawings

WATER-FREE ANTIPERSPIRANT SPRAYS WITH IMPROVED SUBSTANCE

CROSS-REFERENCES TO RELATED APPLICATIONS

This application is a continuation of PCT/EP2010/054099, filed on Mar. 29, 2010, which claims priority under 35 U.S.C. §119 to DE 10 2009 002 098.5 filed on Apr. 1, 2009.

FIELD OF THE INVENTION

The present invention relates to anhydrous antiperspirant compositions, in particular anhydrous suspensions that are sprayable with or without a propellant.

BACKGROUND OF THE INVENTION

In addition to antiperspirant active ingredients, anhydrous antiperspirant suspensions that are sprayable using a propellant typically contain at least one cosmetic oil as a carrier for the particulate antiperspirant active ingredient. The suspensions are packaged in a pressure-resistant container, usually a can of tin plate or aluminum, which is lacquered on the inside, together with a liquefied hydrocarbon, such as n-butane, isobutane and/or propane, as propellant. Before using the spray valve, during which propellant and a proportion of the suspension is released, the container must first be shaken sufficiently to mix in the antiperspirant active ingredient which has settled out. In order to prevent the suspended antiperspirant active ingredient from immediately settling back out, conventional commercial suspensions contain a suspending agent such as hydrophobically modified hectorites, some examples of which may be obtained under the trade names Bentone Gel or Bentone Powder from the companies Rheox and Elementis Specialties.

In conventional commercial sprays, the antiperspirant active ingredient suspended in the anhydrous carrier is covered with a layer of oil. During and after application onto the skin, this oil layer is favorable for the spray pattern. In other words, the active ingredient is not excessively atomized, but instead arrives in a targeted manner on the skin; the oil layer moreover ensures a certain level of adhesion of the pulverulent antiperspirant active ingredient to the skin. This oil layer may, however, delay the release of the antiperspirant active ingredient in its active water-soluble form. In particular, relatively non-polar oils and/or oils with a low solubility parameter contribute to delaying active ingredient release.

Attempts by the present applicant to replace the relatively non-polar oils and/or oils with a low solubility parameter to the greatest possible extent with polar oils and/or oils with a higher solubility parameter have not been met with much success; once the polar oils and/or oils with a higher solubility parameter constituted at least 50 wt. % of the entire carrier oil (excluding propellant), the product was discharged non-uniformly from the spray can and the spray pattern obtained was unsuitable for the intended application.

Cyclomethicone is already known in the prior art as a highly suitable carrier oil for antiperspirant sprays. Despite its low solubility parameter, very satisfactory release of the antiperspirant active ingredient is achieved with cyclomethicone, since this oil has a relatively high volatility and thus does not excessively block the antiperspirant active ingredient.

Due to cyclomethicone's persistence, its use should as far as possible be avoided. It is therefore desirable to formulate anhydrous antiperspirant compositions which exhibit improved active ingredient release of the antiperspirant active ingredient while dispensing to the greatest possible extent with the use of cyclomethicone.

Furthermore, other desirable features and characteristics of the present invention will become apparent from the subsequent detailed description of the invention and the appended claims, taken in conjunction with the background of the invention.

SUMMARY OF THE INVENTION

The above objects and others are met by an antiperspirant composition for personal hygiene, formulated as a suspension which is sprayable with or without a propellant, which includes a) at least one antiperspirant active ingredient, b) 0-5 wt. % of free water, relative to the weight of the composition excluding propellant, c) triethyl citrate, d) at least one further cosmetic oil which is liquid under standard conditions as carrier, and e) 0 to less than 1 wt. % of cyclomethicone, relative to the weight of the composition excluding propellant, wherein the proportion by weight of triethyl citrate in the total quantity of oils c) plus d) plus e), relative to the entire composition excluding propellant, amounts to 13-50 wt. %.

The above objects and others are also met by a method for reducing and/or regulating sweating and/or body odor, in which such an antiperspirant composition is applied in an effective quantity onto the skin, preferably onto the skin in the armpit area.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The antiperspirant compositions according to the invention on an anhydrous basis are formulated as a suspension sprayable with a propellant.

The antiperspirant active ingredient combination according to the invention is preferably suitable for compositions of a sprayable formulation, in particular for suspensions containing propellant which are used as an antiperspirant spray.

For the purposes of the present application, "standard conditions" are a temperature of 20° C. and a pressure of 1013.25 mbar. Melting point data likewise relate to a pressure of 1013.25 mbar.

It has surprisingly now been found that the release of the antiperspirant active ingredient from an anhydrous antiperspirant composition may be improved if the latter contains triethyl citrate and at least one further cosmetic oil which is liquid under standard conditions as a carrier, in which the proportion by weight of triethyl citrate in the total quantity of oils c) plus d) plus e), relative to the entire composition excluding propellant, amounts to 13-50 wt. % and 0 to less than 1 wt. % of cyclomethicone is present.

The present invention accordingly provides antiperspirant compositions for personal hygiene, formulated as a suspension sprayable with a propellant containing at least one antiperspirant active ingredient, 0-5 wt. % of free water, relative to the weight of the composition excluding propellant, furthermore triethyl citrate and at least one further cosmetic oil which is liquid under standard conditions as carrier, in which the proportion by weight of triethyl citrate in the total quantity of oils, relative to the entire composition excluding propellant, amounts to 13-50 wt. %, and 0 to less than 1 wt. % of cyclomethicone, relative to the weight of the composition excluding propellant, is present.

Triethyl citrate is present in the compositions according to the invention in a quantity such that its proportion by weight in the total oil content amounts to 13-50 wt. %. The proportion by weight of triethyl citrate in the total oil content preferably amounts to 15-40 wt. %, particularly preferably to 16-35 wt. %, extremely preferably to 20-30 wt. %.

The total oil content should be taken to mean the weight of the previously mentioned components c) plus d) plus e). The propellant should not be taken into account.

Relative to the weight of the entire composition excluding propellant, triethyl citrate is preferably present in a quantity of 12-35 wt. %, particularly preferably of 19-30 wt. %, extremely preferably of 22-25 wt. %, a content of 13, 14, 15, 16, 17, 18, 20, 21, 23 and 24 wt. % of triethyl citrate, relative to the weight of the entire composition excluding propellant, also possibly being particularly preferred.

In addition to the triethyl citrate, the compositions according to the invention contain at least one further cosmetic oil, in which the proportion by weight of the at least one oil which differs from triethyl citrate in the total quantity of oils, relative to the entire composition excluding propellant, amounts to 50-87 wt. %. The total proportion by weight of all the oils which differ from triethyl citrate in the total quantity of oils, relative to the entire composition excluding propellant, preferably amounts to 60-85 wt. %, particularly preferably to 65-84 wt. %, extremely preferably to 70-80 wt. %.

According to the invention, scents and fragrances do not count among the cosmetic oils which are taken into account when calculating the proportion by weight of triethyl citrate in the total oil content. Examples of scent and fragrance compounds of the ester type are benzyl acetate, phenoxyethyl isobutyrate, p-tert.-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmecyclate. Examples of scent and fragrance compounds of the ether type are benzyl ethyl ether and ambroxan, examples of scent and fragrance compounds of the aldehyde type are the linear alkanals with 8-18 C atoms, citral, citronellal, citronellyloxyacetaldehyde, cyclamen aldehyde, lilial and bourgeonal, examples of scent and fragrance compounds of the ketone type are the ionones, alpha-isomethyl ionone and methyl cedryl ketone, examples of scent and fragrance compounds of the alcohol type are anethole, citronellol, eugenol, geraniol, linalool, phenylethyl alcohol and terpineol, examples of scent and fragrance compounds of the terpene type are limonene and pinene. Examples of scent and fragrance compounds are pine, citrus, jasmine, patchouli, rose, ylang-ylang oil, muscatel sage oil, chamomile oil, clove oil, mint oil, cinnamon leaf oil, lime blossom oil, juniper berry oil, vetiver oil, olibanum oil, galbanum oil, labdanum oil, orange-blossom oil, neroli oil, orange peel oil and sandalwood oil, furthermore essential oils such as angelica root oil, anise oil, arnica blossom oil, basil oil, bay oil, bergamot oil, champak flower oil, silver fir oil, silver fir cone oil, elemi oil, eucalyptus oil, fennel oil, pine-needle oil, geranium oil, ginger grass oil, guaiacwood oil, gurjun balsam oil, helichrysum oil, ho oil, ginger oil, iris oil, cajeput oil, calamus oil, chamomile oil, camphor oil, canaga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, ambrette oil, myrrh oil, clove oil, niaouli oil, orange oil, origanum oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, terpentine oil, thuja oil, thyme oil, verbena oil, juniper berry oil, wormwood oil, wintergreen oil, hyssop oil, cinnamon oil, citronellol, lemon oil and cypress oil. Further scent and fragrance compounds are ambrettolide, α-amylcinnamaldehyde, anethole, anisaldehyde, anisyl alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, methyl heptine carbonate, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl N-amyl ketone, methylanthranilic acid methyl ester, p-methylacetophenone, methylchavicol, p-methylquinoline, methyl β-naphthyl ketone, methyl n-nonylacetaldehyde, methyl n-nonyl ketone, muscone, β-naphthol ethyl ether, β-naphthol methyl ether, nerol, nitrobenzene, n-nonylaldehyde, nonyl alcohol, n-octylaldehyde, p-oxyacetophenone, pentadecanolide, β-phenyl ethyl alcohol, phenylacetaldehyde dimethyl acetal, phenylacetic acid, pulegone, safrole, isoamyl salicylate, methyl salicylate, hexyl salicylate, cyclohexyl salicylate, santalol, skatole, terpineol, thymene, thymol, γ-undecalactone, vanillin, veratrumaldehyde, cinnamaldehyde, cinnamyl alcohol, cinnamic acid, ethyl cinnamate and benzyl cinnamate.

Further (more highly volatile) fragrances are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral and citronellal.

The total quantity of triethyl citrate and at least one further cosmetic oil which is liquid under standard conditions amounts in preferred antiperspirant compositions according to the invention to 30-95 wt. %, preferably to 40-93 wt. %, particularly preferably to 50-90 wt. %, extremely preferably to 55-85 wt. %, in each case relative to the entire composition excluding propellant. A total quantity of triethyl citrate and at least one further cosmetic oil which is liquid under standard conditions of 56, 57, 58, 59, 60, 63, 65, 68, 70, 73, 75, 78 or 80 wt. %, in each case relative to the entire composition excluding propellant, may be particularly preferred according to the invention, a total quantity of 53-63 wt. %, relative to the entire composition excluding propellant, being particularly preferred.

Among the cosmetic oils, a distinction is drawn between volatile and non-volatile oils. Non-volatile oils are taken to mean those oils which, at 20° C. and an ambient pressure of 1013 hPa, exhibit a vapor pressure of less than 2.66 Pa (0.02 mm Hg). Volatile oils are taken to mean those oils which, at 20° C. and an ambient pressure of 1013 hPa, exhibit a vapor pressure of 2.66 Pa-40000 Pa (0.02 mm-300 mm Hg), preferably of 13-12000 Pa (0.1-90 mm Hg), particularly preferably of 15-8000 Pa, extremely preferably of 300-3000 Pa.

The compositions according to the invention are inter alia characterized in that they contain 0 to less than 1 wt. % of cyclomethicone, relative to the weight of the composition excluding propellant.

The INCI name Cyclomethicone is in particular taken to mean cyclotrisiloxane (hexamethylcyclotrisiloxane), cyclotetrasiloxane (octamethylcyclotetrasiloxane), cyclopentasiloxane (decamethylcyclopentasiloxane) and cyclohexasiloxane (dodecamethylcyclohexasiloxane). These oils exhibit a vapor pressure of approx. 13-15 Pa at 20° C.

In a preferred embodiment, the compositions according to the invention are free of volatile linear silicone oils, in particular free of volatile linear silicone oils with 2-10 siloxane units, such as hexamethyldisiloxane ($L_2$), octamethyltrisiloxane ($L_3$), decamethyltetrasiloxane ($L_4$), as are for example present in the commercial products DC 2-1184, Dow Corning® 200 (0.65 cSt) and Dow Corning® 200 (1.5 cSt) from Dow Corning, and in particular free of low molecular weight phenyl trimethicone with a vapor pressure at 20° C. of approx. 2000 Pa, as is for example obtainable from GE Bayer Silicones/Momentive under the name Baysilone Fluid PD 5. Further preferred compositions according to the invention are characterized in that, in addition to triethyl citrate, at least one volatile non-silicone oil is also present because it provides a drier skin feel and more rapid active ingredient release. Preferred volatile non-silicone oils are selected from $C_8$-$C_{16}$ isoparaffins, in particular from isononane, isodecane, isoundecane, isododecane, isotridecane, isotetradecane, isopentadecane, and isohexadecane, and mixtures thereof. $C_{10}$-$C_{13}$ isoparaffin mixtures are preferred, in particular those with a vapor pressure at 20° C. of approx. 300-400 Pa, preferably of 360 Pa. This at least one $C_8$-$C_{16}$ isoparaffin is preferably present in a total quantity of 25-50 wt. %, preferably of 30-45 wt. %, particularly preferably of 32-40 wt. %, extremely preferably of 33, 34, 35, 36, 37, 38 or 39 wt. %, in each case relative to the entire composition excluding propellant.

Compositions which are preferred according to the invention are characterized in that the at least one carrier oil which is liquid under standard conditions comprises at least one volatile $C_8$-$C_{16}$ isoparaffin, in particular isononane, isodecane, isoundecane, isododecane, isotridecane, isotetradecane, isopentadecane and isohexadecane and mixtures thereof.

Further compositions which are preferred according to the invention contain triethyl citrate and at least one $C_8$-$C_{16}$ isoparaffin, selected from isononane, isodecane, isoundecane, isododecane, isotridecane, isotetradecane, isopentadecane and isohexadecane and mixtures of these isoparaffins. Further compositions which are preferred according to the invention contain triethyl citrate and at least one $C_8$-$C_{16}$ isoparaffin, selected from isononane, isodecane, isoundecane, isododecane, isotridecane and mixtures of these $C_8$-$C_{16}$ isoparaffins.

Further compositions which are preferred according to the invention contain triethyl citrate and a mixture of isodecane, isoundecane, isododecane and isotridecane.

In addition to triethyl citrate and the at least one above-stated $C_8$-$C_{16}$ isoparaffin, further antiperspirant compositions which are preferred according to the invention contain at least one non-volatile cosmetic oil, selected from non-volatile silicone oils and non-volatile non-silicone oils. The at least one non-volatile oil offsets the negative effect of the volatile isoparaffin on the residue behavior of antiperspirant compositions which are preferred according to the invention. Thanks to the relatively rapid evaporation of the volatile oils, solid, insoluble components, in particular the antiperspirant active ingredients, may be visible as an unattractive residue on the skin. These residues may be successfully masked with a non-volatile oil. Moreover, parameters such as skin feel, visibility of the residue and stability of the suspension may be finely controlled and better adapted to consumer requirements with a mixture of non-volatile and volatile oil.

It goes without saying that it is likewise possible to formulate antiperspirant compositions according to the invention with a small proportion of volatile oils, i.e. with 0.5-24.5 wt. % of volatile oils, relative to the weight of the composition excluding propellant, or even without volatile oils.

The non-volatile non-silicone oil types stated below are particularly preferred as an accompanying oil for triethyl citrate.

Esters which are particularly preferred according to the invention are those of linear or branched saturated or unsaturated fatty alcohols having 2-30 carbon atoms with linear or branched saturated or unsaturated fatty acids having 2-30 carbon atoms, which may be hydroxylated. Preferred esters are those of linear or branched saturated fatty alcohols having 2-5 carbon atoms with linear or branched saturated or unsaturated fatty acids having 10-18 carbon atoms, which may be hydroxylated. Preferred examples are isopropyl palmitate, isopropyl stearate, isopropyl myristate, hexyldecyl stearate (for example Eutanol® G 16 S), hexyldecyl laurate, isononyl isononanoate, 2-ethylhexyl palmitate (for example Cegesoft® C 24) and 2-ethylhexyl stearate (for example Cetiol® 868). Likewise preferred are isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-hexyl laurate, n-decyl oleate, oleyl oleate, oleyl erucate, erucyl oleate, $C_{12}$-$C_{15}$ alkyl lactate and di-$C_{12}$-$C_{13}$-alkyl malate together with the benzoic acid esters of linear or branched $C_{8-22}$ alkanols. Benzoic acid $C_{12}$-$C_{15}$ alkyl esters, for example obtainable as the commercial product Finsolv® TN ($C_{12}$-$C_{15}$ alkyl benzoate), and benzoic acid isostearyl ester, for example obtainable as Finsolv® SB, ethylhexyl benzoate, for example obtainable as Finsolv® EB, and benzoic acid octyldodecyl ester, for example obtainable as Finsolv® BOD, are particularly preferred.

Correspondingly preferred oil mixtures are triethyl citrate/2-ethylhexyl palmitate, triethyl citrate/hexyldecyl laurate, triethyl citrate/2-ethylhexyl stearate, triethyl citrate/isopropyl myristate, triethyl citrate/isopropyl palmitate, triethyl citrate/2-ethylhexyl laurate, triethyl citrate/$C_{12}$-$C_{15}$ alkyl lactate, triethyl citrate/$C_{12}$-$C_{15}$ alkyl benzoate and triethyl citrate/di-$C_{12}$-$C_{13}$-alkyl malate. Particularly preferred oil mixtures are triethyl citrate/isopropyl myristate, triethyl citrate/isopropyl palmitate and triethyl citrate/$C_{12}$-$C_{15}$ alkyl benzoate.

Further non-volatile non-silicone oils which are preferred according to the invention are selected from branched saturated or unsaturated fatty alcohols having 6-30 carbon atoms. These alcohols are frequently also designated Guerbet alcohols, as they can be obtained by the Guerbet reaction. Preferred alcohol oils are hexyldecanol (Eutanol® G 16, Guerbitol® T 16), octyldodecanol (Eutanol® G, Guerbitol® 20), 2-ethylhexyl alcohol and the commercial products Guerbitol® 18, Isofol® 12, Isofol® 16, Isofol® 24, Isofol® 36, Isocarb® 12, Isocarb® 16 or Isocarb® 24.

Further preferred non-volatile non-silicone oils are selected from mixtures of Guerbet alcohols and Guerbet alcohol esters, for example the commercial product Cetiol® PGL (hexyldecanol and hexyldecyl laurate).

Further non-volatile non-silicone oils which are suitable according to the invention are selected from the triglycerides of linear or branched, saturated or unsaturated, optionally hydroxylated $C_{8-30}$ fatty acids. It may be particularly suitable to use natural oils, for example soy oil, cottonseed oil, sunflower oil, palm oil, palm kernel oil, linseed oil, almond oil, castor oil, corn oil, rapeseed oil, olive oil, sesame oil, thistle oil, wheat germ oil, peach stone oil and the liquid fractions of coconut oil and the like. Synthetic triglyceride oils are, however, also suitable, in particular capric/caprylic triglycerides, for example the commercial products Myritol® 318, Myritol® 331 (Cognis) or Miglyol® 812 (Mils) with unbranched fatty acid residues and glyceryl triisostearin and the commercial products Estol® GTEH 3609 (Uniqema) or Myritol® GTEH (Cognis) with branched fatty acid residues.

Further non-volatile non-silicone oils which are particularly preferred according to the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further non-volatile non-silicone oils which are particularly preferred according to the invention are selected from the addition products of 1 to 5 propylene oxide units onto mono- or polyhydric $C_{3-22}$ alkanols such as octanol, decanol, decanediol, lauryl alcohol, myristyl alcohol and stearyl alcohol, for example PPG-2 myristyl ether and PPG-3 myristyl ether (Witconol® APM).

Further non-volatile non-silicone oils which are particularly preferred according to the invention are selected from the addition products of at least 6 ethylene oxide and/or propylene oxide units onto mono- or polyhydric $C_{3-22}$ alkanols such as glycerol, butanol, butanediol, myristyl alcohol and stearyl alcohol, which may if desired be esterified, for example PPG-14 butyl ether (Ucon Fluid® AP), PPG-9 butyl ether (Breox® B25), PPG-10 butanediol (Macol® 57), PPG-15 stearyl ether (Arlamol® E) and glycereth-7 diisononanoate.

Further non-volatile non-silicone oils which are particularly preferred according to the invention are selected from symmetrical, asymmetrical or cyclic esters of carbonic acid with $C_6$-$C_{20}$ alcohols, for example dicaprylyl carbonate (Cetiol® CC). Esters of carbonic acid with $C_1$-$C_5$ alcohols, for example glycerol carbonate or propylene carbonate, on the other hand, are not compounds which are suitable as cosmetic oil d). Propylene carbonate may nonetheless be present in the compositions according to the invention, primarily as an activator for the lipophilic thickener. The proportion thereof should, however, not be taken into account when calculating the proportion by weight of triethyl citrate in the total quantity of oils c)+d)+e).

Further oils which may be preferred according to the invention are selected from the esters of dimers of unsaturated $C_{12}$-$C_{22}$ fatty acids (dimer fatty acids) with monovalent linear, branched or cyclic $C_2$-$C_{18}$ alkanols or with polyhydric linear or branched $C_2$-$C_6$ alkanols.

In addition to triethyl citrate, it may be preferred according to the invention to use mixtures of the above-stated oils. It is furthermore particularly preferred to use mixtures of triethyl citrate, at least one volatile $C_8$-$C_{16}$ isoparaffin and at least one ester of linear or branched, saturated or unsaturated fatty alcohols having 2-30 carbon atoms with linear or branched saturated or unsaturated fatty acids having 2-30 carbon atoms, which may be hydroxylated. Ethyl esters and isopropyl esters are particularly preferred in such mixtures; isopropyl palmitate and isopropyl myristate are extremely preferred. It is furthermore particularly preferred to use mixtures of triethyl citrate, at least one volatile $C_8$-$C_{16}$ isoparaffin and at least one benzoic acid ester of linear or branched $C_{8-22}$ alkanols.

Oil mixtures which are particularly preferred according to the invention are triethyl citrate/2-ethylhexyl palmitate/isodecane/isoundecane/isododecane/isotridecane, triethyl citrate/hexyldecyl laurate/isodecane/isoundecane/isododecane/isotridecane, triethyl citrate/2-ethylhexyl stearate/isodecane/isoundecane/isododecane/isotridecane, triethyl citrate/isopropyl myristate/isodecane/isoundecane/isododecane/isotridecane, triethyl citrate/isopropyl palmitate/isononane/isodecane/isoundecane/isododecane/isotridecane, triethyl citrate/2-ethylhexyl laurate/isodecane/isoundecane/isododecane/isotridecane, triethyl citrate/$C_{12}$-$C_{15}$ alkyl lactate/isodecane/isoundecane/isododecane/isotridecane, triethyl citrate/$C_{12}$-$C_{15}$ alkyl benzoate/isodecane/isoundecane/isododecane/isotridecane and triethyl citrate/di-$C_{12}$-$C_{13}$-alkyl malate/isodecane/isoundecane/isododecane/isotridecane.

In preferred oil mixtures, all three types of oil (triethyl citrate/ester/$C_8$-$C_{16}$ isoparaffin) are present in identical proportions by weight. Further preferred ratios by weight of triethyl citrate/ester/$C_{8-16}$ isoparaffin are (1-1.3):(0.6-1):(1-3). Further preferred ratios by weight of triethyl citrate/ester/$C_8$-$C_{16}$ isoparaffin are (1-1.3):1:(1-1.5). Further preferred ratios by weight of triethyl citrate/ester/$C_8$-$C_{16}$ isoparaffin are (1-1.3):(0.6-0.9):(2.5-3), in particular 1:0.8:3.

In preferred oil mixtures, all three types of oil (triethyl citrate/isopropyl myristate/$C_8$-$C_{16}$ isoparaffin) are present in identical proportions by weight. Further preferred ratios by weight of triethyl citrate/isopropyl myristate/$C_{8-16}$ isoparaffin are (1-1.3):(0.6-1):(1-3). Further preferred ratios by weight of triethyl citrate/isopropyl myristate/$C_8$-$C_{16}$ isoparaffin are (1-1.3):1:(1-1.5). Further preferred ratios by weight of triethyl citrate/isopropyl myristate/$C_8$-$C_{16}$ isoparaffin are (1-1.3):(0.6-0.9):(2.5-3), in particular 1:0.8:3.

In preferred oil mixtures, all three types of oil (triethyl citrate/isopropyl palmitate/$C_8$-$C_{16}$ isoparaffin) are present in identical proportions by weight. Further preferred ratios by weight of triethyl citrate/isopropyl palmitate/$C_{8-16}$ isoparaffin are (1-1.3):(0.6-1):(1-3). Further preferred ratios by weight of triethyl citrate/isopropyl palmitate/$C_8$-$C_{16}$ isoparaffin are (1-1.3):1:(1-1.5). Further preferred ratios by weight of triethyl citrate/isopropyl palmitate/$C_8$-$C_{16}$ isoparaffin are (1-1.3):(0.6-0.9):(2.5-3), in particular 1:0.8:3.

In preferred oil mixtures, all three types of oil (triethyl citrate/$C_{12}$-$C_{15}$ alkyl benzoate/$C_8$-$C_{16}$ isoparaffin) are present in identical proportions by weight. Further preferred ratios by weight of triethyl citrate/$C_{12}$-$C_{15}$ alkyl benzoate/$C_{8-16}$ isoparaffin are (1-1.3):(0.6-1):(1-3). Further preferred ratios by weight of triethyl citrate/$C_{12}$-$C_{15}$ alkyl benzoate/$C_8$-$C_{16}$ isoparaffin are (1-1.3):1:(1-1.5). Further preferred ratios by weight of triethyl citrate/$C_{12}$-$C_{15}$ alkyl benzoate/$C_8$-$C_{16}$ isoparaffin are (1-1.3):(0.6-0.9):(2.5-3), in particular 1:0.8:3.

In preferred oil mixtures, all three types of oil (triethyl citrate/ester/$C_{10}$-$C_{13}$ isoparaffin) are present in identical proportions by weight. Further preferred ratios by weight of triethyl citrate/ester/$C_{10-13}$ isoparaffin are (1-1.3):(0.6-1):(1-3). Further preferred ratios by weight of triethyl citrate/ester/$C_{10}$-$C_{13}$ isoparaffin are (1-1.3):1:(1-1.5). Further preferred ratios by weight of triethyl citrate/ester/$C_{10}$-$C_{13}$ isoparaffin are (1-1.3):(0.6-0.9):(2.5-3), in particular 1:0.8:3.

In preferred oil mixtures, all three types of oil (triethyl citrate/isopropyl myristate/$C_{10}$-$C_{13}$ isoparaffin) are present in identical proportions by weight. Further preferred ratios by weight of triethyl citrate/isopropyl myristate/$C_{10-13}$ isoparaffin are (1-1.3):(0.6-1):(1-3). Further preferred ratios by weight of triethyl citrate/isopropyl myristate/$C_{10}$-$C_{13}$ isoparaffin are (1-1.3):1:(1-1.5). Further preferred ratios by weight of triethyl citrate/isopropyl myristate/$C_{10}$-$C_{13}$ isoparaffin are (1-1.3):(0.6-0.9):(2.5-3), in particular 1:0.8:3.

In preferred oil mixtures, all three types of oil (triethyl citrate/isopropyl palmitate/$C_{10}$-$C_{13}$ isoparaffin) are present in identical proportions by weight. Further preferred ratios by weight of triethyl citrate/isopropyl palmitate/$C_{10-13}$ isoparaffin are (1-1.3):(0.6-1):(1-3). Further preferred ratios by weight of triethyl citrate/isopropyl palmitate/$C_{10}$-$C_{13}$ isoparaffin are (1-1.3):1:(1-1.5). Further preferred ratios by weight of triethyl citrate/isopropyl palmitate/$C_{10}$-$C_{13}$ isoparaffin are (1-1.3):(0.6-0.9):(2.5-3), in particular 1:0.8:3.

In preferred oil mixtures, all three types of oil (triethyl citrate/$C_{12}$-$C_{15}$ alkyl benzoate/$C_{10}$-$C_{13}$ isoparaffin) are present in identical proportions by weight. Further preferred ratios by weight of triethyl citrate/$C_{12}$-$C_{15}$ alkyl benzoate/$C_{10-13}$ isoparaffin are (1-1.3):(0.6-1):(1-3). Further preferred ratios by weight of triethyl citrate/$C_{12}$-$C_{15}$ alkyl benzoate/$C_{10}$-$C_{13}$ isoparaffin are (1-1.3):1:(1-1.5). Further preferred ratios by weight of triethyl citrate/$C_{12}$-$C_{15}$ alkyl benzoate/$C_{10}$-$C_{13}$ isoparaffin are (1-1.3):(0.6-0.9):(2.5-3), in particular 1:0.8:3.

It has furthermore been found that the release of the antiperspirant active ingredient from an antiperspirant composition according to the invention may be improved still further if at least one organosiloxane-oxyalkylene copolymer is present. Compositions which are preferred according to the invention are characterized in that the organosiloxane-oxyalkylene copolymer is selected from compounds of the general structural formulae (I), (II), (III), (IV) and (V),

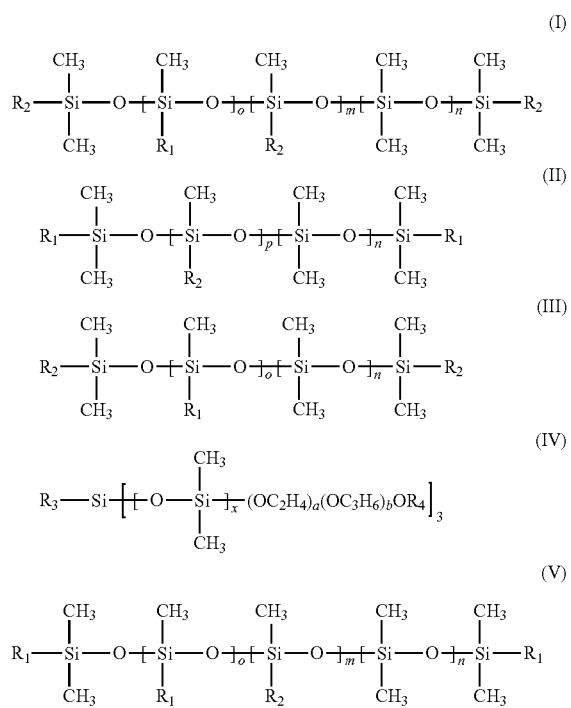

in which the residues $R^1$ mutually independently represent a linear or branched $C_1$-$C_{30}$ alkyl group or an optionally substituted phenyl group, preferably a methyl group, the residues $R^2$ mutually independently represent the groups —$C_cH_{2c}$—O—($C_2H_4O$—)$_a$($C_3H_6O$—)$_b R^5$ or —$C_cH_{2c}$—O—($C_2H_4O$—)$_a R^5$ or —$CH_2$—$CH(CH_3)$—$CH_2$—O—($C_2H_4O$—)$_a$($C_3H_6O$—)$_b R^5$, the residues $R^3$ and $R^4$ mutually independently represent a linear or branched $C_1$-$C_{16}$ alkyl group and preferably methyl groups, the residues $R^5$ represent a hydrogen atom or a methyl group, m represents a number from 0-20, n represent a number from 0-500, preferably 20-400, particularly preferably 50-300, o represents a number from 0-20, p represents a number from 1-50, preferably 10-40, particularly preferably 20-30, a represents a number from 0-50, preferably 5-25, particularly preferably 7-22, b represents a number from 0-50, preferably either 0 or 5-30, particularly preferably either 0 or 10-25, extremely preferably either 0 or 24, a+b are at least 1, c represents a number from 1-4, particularly preferably 3, and x represents a number from 1-100.

Such organosiloxane-oxyalkylene copolymers which are preferred for the teaching according to the invention (composition, use, method) are those of the above general structural formulae (I), (II), (III) and (V), in which the residues $R^1$ mutually independently represent a linear or branched $C_1$-$C_{30}$ alkyl group, preferably a linear or branched $C_1$-$C_{16}$ alkyl group, particularly preferably a linear or branched $C_1$-$C_4$ alkyl group, extremely preferably a methyl group. Particularly preferred linear or branched $C_1$-$C_4$ alkyl groups are selected from methyl, ethyl, 1-methylethyl, n-propyl, n-butyl, tert.-butyl and 2-methylpropyl.

Such organosiloxane-oxyalkylene copolymers which are furthermore preferred for the teaching according to the invention (composition, use, method) are those of above general structural formula (IV), in which the residues $R^3$ and $R^4$ mutually independently represent a linear or branched $C_1$-$C_{16}$ alkyl group, preferably a linear or branched $C_1$-$C_6$ alkyl group, particularly preferably a linear or branched $C_1$-$C_4$ alkyl group, extremely preferably a methyl group. Particularly preferred linear or branched $C_1$-$C_4$ alkyl groups are selected from methyl, ethyl, 1-methylethyl, n-propyl, n-butyl, tert.-butyl and 2-methylpropyl.

Further compositions which are preferred according to the invention are characterized in that the organosiloxane-oxyalkylene copolymer of the above general structural formulae (I), (II), (III), (IV) and (V) has an HLB value in the range from 8-20, preferably from 10-18, particularly preferably from 11-16.

Further compositions which are preferred according to the invention are characterized in that the organosiloxane-oxyalkylene copolymer of the above general structural formulae (I), (II), (III) and (V), in which the residues $R^1$ mutually independently represent a linear or branched $C_1$-$C_{30}$ alkyl group, preferably a linear or branched $C_1$-$C_{16}$ alkyl group, particularly preferably a linear or branched $C_1$-$C_4$ alkyl group, in particular methyl, ethyl, 1-methylethyl, n-propyl, n-butyl, tert.-butyl and 2-methylpropyl, extremely preferably a methyl group, and have an HLB value in the range from 8-20, preferably from 10-18, particularly preferably from 11-16.

Further compositions which are preferred according to the invention are characterized in that the organosiloxane-oxyalkylene copolymer of the above general structural formula (IV), in which the residues $R^3$ and $R^4$ mutually independently represent a linear or branched $C_1$-$C_{16}$ alkyl group, preferably a linear or branched $C_1$-$C_6$ alkyl group, particularly preferably a linear or branched $C_1$-$C_4$ alkyl group, in particular methyl, ethyl, 1-methylethyl, n-propyl, n-butyl, tert.-butyl and 2-methylpropyl, extremely preferably a methyl group, and have an HLB value in the range from 8-20, preferably from 10-18, particularly preferably from 11-16.

Compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl group, $R^2$=—$C_cH_{2c}$—O—($C_2H_4O$—)$_a R^5$,
$R^5$=a hydrogen atom or a methyl group,
n=0, p=1, a=5-20, preferably 7-15, particularly preferably 8-11, b=0, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl group, $R^2$=—$C_cH_{2c}$—O—$(C_2H_4O—)_aR^5$, $R^5$=a hydrogen atom, n=0, p=1, b=0, a=7, 8, 9, 10, 11, 12, 13, 14 or 15, c=3, preferably selected from

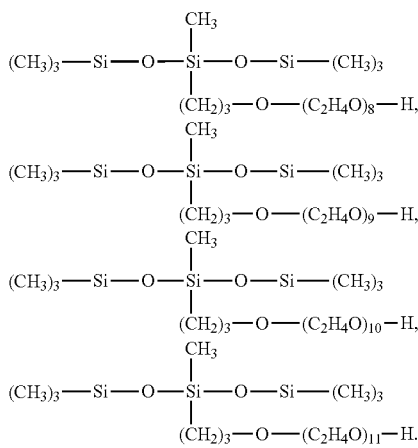

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=tert.-butyl group, $R^2$=—$C_cH_{2c}$—O—$(C_2H_4O—)_aR^5$, $R^5$=a hydrogen atom or a methyl group, n=0, p=1, a=5-20, preferably 7-15, particularly preferably 8-11, b=0, c=3, preferably selected from

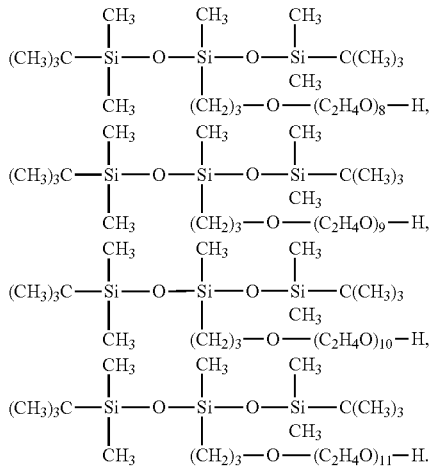

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=tert.-butyl groups, $R^2$=—$C_cH_{2c}$—O—$(C_2H_4O—)_aR^5$, $R^5$=a hydrogen atom, n=0, p=1, a=7, 8, 9, 10, 11, 12, 13, 14 or 15, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=isopropyl groups (—$CH(CH_3)_2$), $R^2$=—$C_cH_{2c}$—O—$(C_2H_4O—)_aR^5$, $R^5$=a hydrogen atom or a methyl group, n=0, p=1, a=5-20, preferably 7-15, particularly preferably 8-11, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=isopropyl groups (—$CH(CH_3)_2$), $R^2$=—$C_cH_{2c}$—O—$(C_2H_4O—)_aR^5$, $R^5$=a hydrogen atom, n=0, p=1, a=7, 8, 9, 10, 11, 12, 13, 14 or 15, c=3, preferably selected from

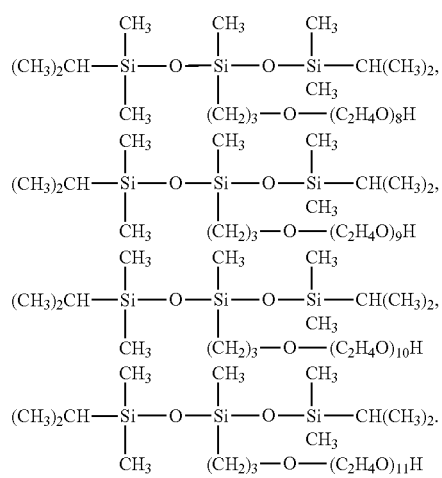

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl, $R^2$=—$CH_2$—$CH(CH_3)$—$CH_2$—O—$(C_2H_4O—)_aR^5$, $R^5$=a hydrogen atom or a methyl group, n=0, p=1, a=5-20, preferably 7-15, particularly preferably 8-11, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl, $R^2$=—$CH_2$—$CH(CH_3)$—$CH_2$—O—$(C_2H_4O—)_aR^5$, $R^5$=a hydrogen atom, n=0, p=1, a=7, 8, 9, 10, 11, 12, 13, 14 or 15, c=3, preferably selected from

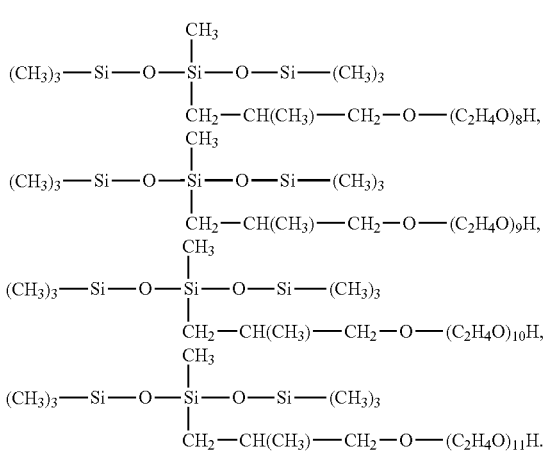

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$, $R^5$=a hydrogen atom or a methyl group, n=10-500, preferably 20-400, particularly preferably 50-300, p=10-50, a=5-30, preferably 10-25, particularly preferably 22, b=5-30, preferably 10-25, particularly preferably 24, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$, $R^5$=a hydrogen atom, n=10-500, preferably 20-400, particularly preferably 50-300, p=10-50, preferably 15-40, particularly preferably 20-30, a=5-30, preferably 10-25, particularly preferably 22, b=5-30, preferably 10-25, particularly preferably 24, c=3.

Further compositions which are particularly preferred according to the invention are characterized in that the organosiloxane-oxyalkylene copolymer is selected from compounds of the general structural formula (II) with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$, $R^5$=a hydrogen atom, n=10-500, preferably 20-400, particularly preferably 50-300, p=10-50, preferably 15-40, particularly preferably 20-30, a=5-30, preferably 10-25, particularly preferably 22, b=5-30, c=3.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=18, b=18, c=3, $R^5$=methyl, n=10-500, p=10-50.

One such organosiloxane-oxyalkylene copolymer is for example obtainable under the tradename Dow Corning 190 (INCI: PEG/PPG-18/18 Dimethicone).

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=12, b=0, c=3, $R^5$=methyl, n=10-500, p=10-50.

One such organosiloxane-oxyalkylene copolymer is for example obtainable under the tradename Dow Corning 193 (INCI: PEG-12 Dimethicone).

Dow Corning 193 (PEG-12 Dimethicone) may exhibit odor instability under certain conditions.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=7, b=0, c=2, $R^5$=methyl, n=0, p=1.

Such an organosiloxane-oxyalkylene copolymer is for example obtainable under the tradename Silwet L-77.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=22, b=24, c=3, $R^5$=methyl, n=10-500, p=10-50=—$(CH_2)_3$—O—$(C_2H_4O—)_{22}(C_3H_6O—)_{24}$—$CH_3$.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=17, b=18, c=3, $R^5$=methyl, n=10-500, p=10-50.

Such an organosiloxane-oxyalkylene copolymer is for example obtainable under the tradename Dow Corning Q2-5220 (INCI: PEG/PPG-17/18 Dimethicone).

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=20, b=6, c=3, $R^5$=methyl, n=10-500, p=5-50.

One such organosiloxane-oxyalkylene copolymer is for example obtainable under the tradename Abil B 88184 (INCI: PEG/PPG-20/6 Dimethicone).

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=14, b=4, c=3, $R^5$=methyl, n=10-500, p=5-50.

One such organosiloxane-oxyalkylene copolymer is for example obtainable under the tradename Abil B 8851 (INCI: PEG/PPG-14/4 Dimethicone).

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=tert.-butyl, $R^2$=—$C_cH_{2c}$—O—$(C_2H_4O—)_a$ $(C_3H_6O—)_bR^5$ with a=11, b=0, c=3, $R^5$=H, n=0, p=1.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=isopropyl (—$CH(CH_3)_2$), $R^2$=—$C_cH_{2c}$—O— $(C_2H_4O—)_a(C_3H_6O—)_bR^5$ with a=11, b=0, c=3, $R^5$=H, n=0, p=1.

Further compositions which are preferred according to the invention are characterized in that at least one organosiloxane-oxyalkylene copolymer of the general structural formula (II) is present with an HLB value in the range from 8-20, preferably from 10-18, particularly preferably from 11-16, and with $R^1$=methyl, $R^2$=—$CH_2$—$CH(CH_3)$—$CH_2$—O— $(C_2H_4O—)_a(C_3H_6O—)_bR^5$ with a=8, b=0, $R^5$=H, n=0, p=1.

Further compositions which are preferred according to the invention are characterized in that at least one organosiloxane-oxyalkylene copolymer of the general structural formula (I) is present with an HLB value in the range from 8-20, preferably from 10-18, particularly preferably from 11-16, and with $R^1$=methyl, $R^2$=—$C_cH_{2c}$—O—$(C_2H_4O—)_a(C_3H_6O—)_b$ $R^5$ with a=20, b=20, c=3, $R^5$=methyl, m=0, n=10-500.

One such organosiloxane-oxyalkylene copolymer is for example obtainable under the tradename Abil B 8832 (INCI: Bis-PEG/PPG-20/20 Dimethicone).

A further preferred organosiloxane-oxyalkylene copolymer is Bis-PEG/PPG-16/16 PEG/PPG-16/16 Dimethicone.

Particularly preferred organosiloxane-oxyalkylene copolymers are those explicitly listed above of the general structural formula (II), which bring about better active ingredient release in comparison with the organosiloxane-oxyalkylene copolymers of the general structural formula (I).

Further organosiloxane-oxyalkylene copolymers which are particularly preferred according to the invention are selected from linear polysiloxane-polyoxyalkylene block copolymers, in particular from linear polysiloxane-polyoxyethylene-polyoxypropylene block copolymers. A linear polysiloxane-polyoxyethylene-polyoxypropylene block copolymer with the INCI name PEG/PPG-22/24 Dimethicone is extremely preferred according to the invention. Such a linear polysiloxane-polyoxyethylene-polyoxypropylene block copolymer is for example obtainable under the tradename Mirasil DMCO (INCI: PEG/PPG-22/24 Dimethicone) from Rhodia.

A further preferred linear polysiloxane-polyoxyethylene-polyoxypropylene block copolymer of this type has the INCI name PEG/PPG-10/2 Dimethicone. It is for example obtainable under the tradename Mirasil DMCP 93 (INCI: PEG/PPG-10/2 Dimethicone) from Rhodia.

Further compositions which are particularly preferred according to the invention are characterized in that the organosiloxane-oxyalkylene copolymer is selected from PEG/PPG-18/18 Dimethicone, PEG-12 Dimethicone, PEG/PPG-22/24 Dimethicone, PEG/PPG-17/18 Dimethicone, PEG/PPG-20/6 Dimethicone, PEG/PPG-14/4 Dimethicone, Bis-PEG/PPG-16/16 PEG/PPG-16/16 Dimethicone and mixtures thereof.

Further compositions which are particularly preferred according to the invention are characterized in that they contain PEG/PPG-22/24 Dimethicone and PEG-12 Dimethicone.

Further compositions which are particularly preferred according to the invention are characterized in that they contain PEG/PPG-22/24 Dimethicone and PEG/PPG-20/6 Dimethicone.

Further compositions which are particularly preferred according to the invention are characterized in that they contain PEG/PPG-22/24 Dimethicone and PEG/PPG-14/4 Dimethicone.

Further compositions which are particularly preferred according to the invention are characterized in that they contain PEG/PPG-22/24 Dimethicone and PEG/PPG-17/18 Dimethicone.

Further compositions which are particularly preferred according to the invention are characterized in that they contain PEG/PPG-22/24 Dimethicone and Bis-PEG/PPG-20/20 Dimethicone.

Extremely preferred compositions according to the invention are those which contain PEG/PPG-22/24 Dimethicone and PEG/PPG-20/6 Dimethicone.

Extremely preferred compositions according to the invention are furthermore those which contain PEG/PPG-22/24 Dimethicone and PEG/PPG-14/4 Dimethicone.

Extremely preferred compositions according to the invention are furthermore those which contain PEG/PPG-22/24 Dimethicone and PEG/PPG-17/18 Dimethicone.

Further compositions which are particularly preferred according to the invention are characterized in that they contain PEG-12 Dimethicone and PEG/PPG-20/6 Dimethicone.

Further compositions which are particularly preferred according to the invention are characterized in that they contain PEG-12 Dimethicone and PEG/PPG-14/4 Dimethicone.

Further compositions which are particularly preferred according to the invention are characterized in that they contain PEG-12 Dimethicone and PEG/PPG-17/18 Dimethicone.

Further compositions which are particularly preferred according to the invention are characterized in that they contain PEG-12 Dimethicone and Bis-PEG/PPG-20/20 Dimethicone.

Extremely preferred compositions according to the invention are those which contain PEG-12 Dimethicone and PEG/PPG-20/6 Dimethicone.

Extremely preferred compositions according to the invention are furthermore those which contain PEG-12 Dimethicone and PEG/PPG-17/18 Dimethicone.

Further compositions which are particularly preferred according to the invention are characterized in that they contain PEG/PPG-20/6 Dimethicone and PEG/PPG-14/4 Dimethicone.

Further compositions which are particularly preferred according to the invention are characterized in that they contain PEG/PPG-20/6 Dimethicone and PEG/PPG-17/18 Dimethicone.

Further compositions which are particularly preferred according to the invention are characterized in that they contain PEG/PPG-20/6 Dimethicone and Bis-PEG/PPG-20/20 Dimethicone.

Further compositions which are particularly preferred according to the invention are characterized in that they contain PEG/PPG-14/4 Dimethicone and PEG/PPG-17/18 Dimethicone.

Further compositions which are particularly preferred according to the invention are characterized in that they contain PEG/PPG-14/4 Dimethicone and Bis-PEG/PPG-20/20 Dimethicone.

Further compositions which are particularly preferred according to the invention are characterized in that they contain PEG/PPG-17/18 Dimethicone and Bis-PEG/PPG-20/20 Dimethicone.

Further compositions which are preferred according to the invention are characterized in that the organosiloxane-oxyalkylene copolymer exhibits a water solubility of at least 2 g per 100 g of aqueous solution.

Compositions which are particularly preferred according to the invention are characterized in that the organosiloxane-oxyalkylene copolymer exhibits a water solubility of at least 5 g per 100 g of aqueous solution.

Further compositions which are preferred according to the invention are characterized in that the organosiloxane-oxyalkylene copolymer is at least 2 wt. % miscible with water.

Further compositions which are particularly preferred are characterized in that the organosiloxane-oxyalkylene copolymer is at least 5 wt. % miscible with water.

All the above details regarding water solubility or water miscibility relate to a temperature of 20° C. and a pressure of 1013.25 mbar.

Further preferred compositions contain triethyl citrate and at least one $C_8$-$C_{16}$ isoparaffin, selected from isononane, isodecane, isoundecane, isododecane, isotridecane, isotetradecane, isopentadecane and isohexadecane and mixtures of these isoparaffins, and, as third mandatory component, the linear polysiloxane-polyoxyethylene-polyoxypropylene block copolymer PEG/PPG-22/24 Dimethicone. The name "PEG/PPG-22/24 Dimethicone" used hereinafter always means the linear polysiloxane-polyoxyethylene-polyoxypropylene block copolymer PEG/PPG-22/24 Dimethicone.

Further preferred compositions contain triethyl citrate and a mixture of isodecane, isoundecane, isododecane and isotridecane and the linear polysiloxane-polyoxyethylene-polyoxypropylene block copolymer PEG/PPG-22/24 Dimethicone.

Further preferred compositions contain one of the following mixtures: triethyl citrate/2-ethylhexyl palmitate/PEG/PPG-22/24 Dimethicone, triethyl citrate/hexyldecyl laurate/PEG/PPG-22/24 Dimethicone, triethyl citrate/2-ethylhexyl stearate/PEG/PPG-22/24 Dimethicone, triethyl citrate/isopropyl myristate/PEG/PPG-22/24 Dimethicone, triethyl citrate/isopropyl palmitate/PEG/PPG-22/24 Dimethicone, triethyl citrate/2-ethylhexyl laurate/PEG/PPG-22/24 Dimethicone, triethyl citrate/$C_{12}$-$C_{15}$ alkyl lactate/PEG/PPG-22/24 Dimethicone, triethyl citrate/$C_{12}$-$C_{15}$ alkyl benzoate/PEG/PPG-22/24 Dimethicone, triethyl citrate/di-$C_{12}$-$C_{13}$-alkyl malate/PEG/PPG-22/24 Dimethicone.

Mixtures of triethyl citrate, at least one volatile $C_8$-$C_{16}$ isoparaffin and at least one ester of linear or branched saturated or unsaturated monovalent fatty alcohols having 2-30 carbon atoms with linear or branched saturated or unsaturated fatty acids having 2-30 carbon atoms, which may be hydroxylated, and PEG/PPG-22/24 Dimethicone are furthermore preferred. Ethyl esters and isopropyl esters are particularly preferred in such mixtures; isopropyl palmitate and isopropyl myristate are extremely preferred. Mixtures of triethyl citrate, at least one volatile $C_8$-$C_{16}$ isoparaffin and at least one benzoic acid ester of linear or branched $C_{8-22}$ alkanols and PEG/PPG-22/24 Dimethicone are furthermore preferred.

Mixtures which are particularly preferred according to the invention are triethyl citrate/2-ethylhexyl palmitate/isodecane/isoundecane/isdodecane/isotridecane/PEG/PPG-22/24 Dimethicone, triethyl citrate/hexyldecyl laurate/isodecane/isoundecane/isododecane/isotridecane/PEG/PPG-22/24 Dimethicone, triethyl citrate/2-ethylhexyl stearate/isodecane/isoundecane/isododecane/isotridecane/PEG/PPG-22/24 Dimethicone, triethyl citrate/isopropyl myristate/isodecane/isoundecane/isododecane/isotridecane/PEG/PPG-22/24 Dimethicone, triethyl citrate/isopropyl palmitate/isononane/isodecane/isoundecane/isododecane/isotridecane/PEG/PPG-22/24 Dimethicone, triethyl citrate/2-ethylhexyl laurate/isodecane/isoundecane/isododecane/isotridecane/PEG/PPG-22/24 Dimethicone, triethyl citrate/$C_{12}$-$C_{15}$ alkyl lactate/isodecane/isoundecane/isododecane/isotridecane/PEG/PPG-22/24 Dimethicone, triethyl citrate/$C_{12}$-$C_{15}$ alkyl benzoate/isodecane/isoundecane/isododecane/isotridecane/PEG/PPG-22/24 Dimethicone and triethyl citrate/di-$C_{12}$-$C_{13}$-alkyl malate/isodecane/isoundecane/isododecane/isotridecane/PEG/PPG-22/24 Dimethicone.

Further preferred compositions contain triethyl citrate and at least one $C_8$-$C_{16}$ isoparaffin, selected from isononane, isodecane, isoundecane, isododecane, isotridecane, isotetradecane, isopentadecane and isohexadecane and mixtures of these isoparaffins, and, as third mandatory component, the linear polysiloxane-polyoxyethylene-polyoxypropylene block copolymer PEG/PPG-10/2 Dimethicone. The name "PEG/PPG-10/2 Dimethicone" used hereinafter always means the linear polysiloxane-polyoxyethylene-polyoxypropylene block copolymer PEG/PPG-10/2 Dimethicone.

Further preferred compositions contain triethyl citrate and a mixture of isodecane, isoundecane, isododecane and isotridecane and the linear polysiloxane-polyoxyethylene-polyoxypropylene block copolymer PEG/PPG-10/2 Dimethicone.

Further preferred compositions contain one of the following mixtures: triethyl citrate/2-ethylhexyl palmitate/PEG/PPG-10/2 Dimethicone, triethyl citrate/hexyldecyl laurate/PEG/PPG-10/2 Dimethicone, triethyl citrate/2-ethylhexyl stearate/PEG/PPG-10/2 Dimethicone, triethyl citrate/isopropyl myristate/PEG/PPG-10/2 Dimethicone, triethyl citrate/isopropyl palmitate/PEG/PPG-10/2 Dimethicone, triethyl citrate/2-ethylhexyl laurate/PEG/PPG-10/2 Dimethicone, triethyl citrate/$C_{12}$-$C_{15}$ alkyl lactate/PEG/PPG-10/2 Dimethicone, triethyl citrate/$C_{12}$-$C_{15}$ alkyl benzoate/PEG/PPG-10/2 Dimethicone, triethyl citrate/di-$C_{12}$-$C_{13}$-alkyl malate/PEG/PPG-10/2 Dimethicone.

Mixtures of triethyl citrate, at least one volatile $C_8$-$C_{16}$ isoparaffin and at least one ester of linear or branched saturated or unsaturated monovalent fatty alcohols having 2-30 carbon atoms with linear or branched saturated or unsaturated fatty acids having 2-30 carbon atoms, which may be hydroxylated, and PEG/PPG-10/2 Dimethicone are furthermore preferred. Ethyl esters and isopropyl esters are particularly preferred in such mixtures; isopropyl palmitate and isopropyl myristate are extremely preferred. Mixtures of triethyl citrate, at least one volatile $C_8$-$C_{16}$ isoparaffin and at least one benzoic acid ester of linear or branched $C_{8-22}$ alkanols and PEG/PPG-10/2 Dimethicone are furthermore preferred.

Mixtures which are particularly preferred according to the invention are triethyl citrate/2-ethylhexyl palmitate/isodecane/isoundecane/isododecane/isotridecane/PEG/PPG-10/2

Dimethicone, triethyl citrate/hexyldecyl laurate/isodecane/isoundecane/isododecane/isotridecane/PEG/PPG-10/2 Dimethicone, triethyl citrate/2-ethylhexyl stearate/isodecane/isoundecane/isododecane/isotridecane/PEG/PPG-10/2 Dimethicone, triethyl citrate/isopropyl myristate/isodecane/isoundecane/isododecane/isotridecane/PEG/PPG-10/2 Dimethicone, triethyl citrate/isopropyl palmitate/isononane/isodecane/isoundecane/isododecane/isotridecane/PEG/PPG-10/2 Dimethicone, triethyl citrate/2-ethylhexyl laurate/isodecane/isoundecane/isododecane/isotridecane/PEG/PPG-10/2 Dimethicone, triethyl citrate/$C_{12}$-$C_{15}$ alkyl lactate/isodecane/isoundecane/isododecane/isotridecane/PEG/PPG-10/2 Dimethicone, triethyl citrate/$C_{12}$-$C_{15}$ alkyl benzoate/isodecane/isoundecane/isododecane/isotridecane/PEG/PPG-10/2 Dimethicone and triethyl citrate/di-$C_{12}$-$C_{13}$-alkyl malate/isodecane/isoundecane/isododecane/isotridecane/PEG/PPG-10/2 Dimethicone.

Further compositions which are preferred according to the invention contain at least one of the above-designated organosiloxane-oxyalkylene copolymers in a total quantity of 0.01-5 wt. %, preferably of 0.1-3 wt. %, particularly preferably of 0.5-2 wt. %, extremely preferably of 0.7-1.5 wt. %, in each case relative to the total weight of the composition excluding propellant. The proportion of organosiloxane-oxyalkylene copolymers is not taken into account when calculating the proportion by weight of triethyl citrate in the total quantity of oils c)+d)+e).

The antiperspirant active ingredients and any further active ingredients which are insoluble in the carrier are suspended in an oil mixture c)+d) (+optionally e)) which is liquid under standard conditions. At least one lipophilic thickener is preferably added to this suspension as a suspension auxiliary in order to enhance applicability. Further preferred compositions according to the invention are therefore characterized in that they contain at least one lipophilic thickener.

Compositions which are preferred according to the invention are characterized in that the at least one lipophilic thickener is selected from hydrophobized clay minerals, pyrogenic silicas, bentone gels, ethylene/propylene/styrene copolymers, butylene/ethylene/styrene copolymers, dextrin esters, silicone elastomers, waxes which are solid under standard conditions and/or glycerol triesters. Hydrophobized clay minerals are particularly preferred among these. Preferred hydrophobized clay minerals are selected from hydrophobized montmorillonites, hydrophobized hectorites and hydrophobized bentonites, particularly preferably from Disteardimonium Hectorite, Stearalkonium Hectorite, Quatemium-18 Hectorite and Quatemium-18 Bentonite. Conventional commercial thickeners provide these hydrophobized clay minerals as powders or in the form of a gels in a oil component. Such powders or gels are for example obtainable under the tradename Bentone® or Thixogel.

Compositions which are preferred according to the invention are characterized in that they contain at least one hydrophobized clay mineral in a total quantity of 0.5-10 wt. %, preferably of 1-7 wt. %, particularly preferably of 2-6 wt. %, extremely preferably of 3-5 wt. %, in each case relative to the total weight of the composition excluding propellant. Such hydrophobized clay minerals conventionally require water, ethanol or propylene carbonate as activator in a quantity of 0.3-3 wt. %, preferably of 0.5-2 wt. %, in each case relative to the total weight of the composition excluding propellant according to the invention.

Further lipophilic thickeners which are preferred according to the invention are selected from pyrogenic silicas, for example the commercial products of the Aerosil® series from Evonik Degussa. Hydrophobized pyrogenic silicas are particularly preferred; Silica Silylate and Silica Dimethyl Silylate are extremely preferred.

Compositions which are preferred according to the invention are characterized in that they contain at least one pyrogenic silica, preferably at least one hydrophobized pyrogenic silica, in a total quantity of 0.5-10 wt. %, preferably of 0.8-5 wt. %, particularly preferably of 1-4 wt. %, extremely preferably of 1.5-2 wt. %, in each case relative to the total weight of the composition excluding propellant according to the invention.

Further compositions which are preferred according to the invention are characterized in that they contain at least one hydrophobized pyrogenic silica and at least one hydrophilic silica.

The compositions according to the invention contain at least one antiperspirant active ingredient.

Preferred antiperspirant active ingredients are selected from water-soluble astringent inorganic and organic salts of aluminum and zinc or any desired mixtures of these salts. According to the invention, aluminosilicates and zeolites are not included among the antiperspirant active ingredients.

According to the invention, water solubility is taken to mean solubility of at least 5 wt. % at 20° C., i.e. that quantities of at least 5 g of the antiperspirant active ingredient are soluble in 95 g of water at 20° C.

Particularly preferred antiperspirant active ingredients are selected from aluminum chlorohydrate, in particular aluminum chlorohydrate of the general formula $[Al_2(OH)_5Cl.1\text{-}6H_2O]_n$, preferably $[Al_2(OH)_5Cl.2\text{-}3H_2O]_n$, which may be present in non-activated or in activated (depolymerized) form, together with aluminum chlorohydrate of the general formula $[Al_2(OH)_4Cl_2.1\text{-}6H_2O]_n$, preferably $[Al_2(OH)_4Cl_2.2\text{-}3H_2O]_n$, which may be present in non-activated or in activated (depolymerized) form.

The production of preferred antiperspirant active ingredients is disclosed, for example, in U.S. Pat. Nos. 3,887,692, 3,904,741, 4,359,456, GB 2048229 and GB 1347950.

Furthermore preferred are aluminum sesquichlorohydrate, aluminum dichlorohydrate, aluminum chlorohydrex-propylene glycol (PG) or aluminum chlorohydrex-polyethylene glycol (PEG), aluminum-glycol complexes, for example aluminum-propylene glycol complexes, aluminum sesquichlorohydrex-PG or aluminum sesquichlorohydrex-PEG, aluminum-PG-dichlorohydrex or aluminum-PEG-dichlorohydrex, aluminum hydroxide, furthermore selected from potassium aluminum sulfate ($KAl(SO_4)_2.12H_2O$, alum), aluminum undecylenoyl collagen amino acid, sodium-aluminum lactate+aluminum sulfate, sodium-aluminum chlorohydroxylactate, aluminum bromohydrate, aluminum chloride, the complexes of zinc and sodium salts, the aluminum salts of lipoamino acids, aluminum sulfate, aluminum lactate, aluminum chlorohydroxyallantoinate, sodium-aluminum chlorohydroxylactate, zinc chloride, zinc sulfocarbolate and zinc sulfate.

Antiperspirant active ingredients which are particularly preferred according to the invention are selected from "activated" aluminum salts, which are also designated "enhanced activity" antiperspirant active ingredients. Such active ingredients are known in the prior art and are also commercially obtainable. The production thereof is disclosed, for example, in GB 2048229, U.S. Pat. Nos. 4,775,528 and 6,010,688. Activated aluminum salts are generally produced by heat treating a relatively dilute solution of the salt (for example approx. 10 wt. % salt), in order to enlarge its HPLC peak 4:peak 3 area ratio. The activated salt may then be dried, in particular spray-dried, to yield a powder. As well as spray drying, roller drying is, for example, also suitable.

Activated aluminum salts typically have an HPLC peak 4:peak 3 area ratio of at least 0.4, preferably of at least 0.7, particularly preferably of at least 0.9, at least 70% of the aluminum being attributable to these peaks.

Activated aluminum salts need not necessarily be used as a spray-dried powder.

Further preferred antiperspirant active ingredients are basic calcium-aluminum salts, as are for example disclosed in U.S. Pat. No. 2,571,030. These salts are produced by reacting calcium carbonate with aluminum chlorohydroxide or aluminum chloride and aluminum powder or by adding calcium chloride dihydrate to aluminum chlorohydrate.

Further preferred antiperspirant active ingredients are activated aluminum salts, as are for example disclosed in U.S. Pat. Nos. 6,245,325 or 6,042,816, containing 5-78 wt. % (USP) of an activated antiperspirant aluminum salt, an amino acid or hydroxyalkanoic acid in a quantity such as to provide an (amino acid or hydroxyalkanoic acid) to aluminum weight ratio of 2:1-1:20 and preferably of 1:1 to 1:10, together with a water-soluble calcium salt in a quantity such as to provide a Ca:Al weight ratio of 1:1-1:28 and preferably of 1:2-1:25.

Particularly preferred solid activated antiperspirant salt compositions, for example according to U.S. Pat. Nos. 6,245,325 or 6,042,816, contain 48-78 wt. % (USP), preferably 66-75 wt. % of an activated aluminum salt and 1-16 wt. %, preferably 4-13 wt. % of molecularly bound water (water of hydration), furthermore water-soluble calcium salt in a quantity such that the Ca:Al weight ratio amounts to 1:1-1:28, preferably to 1:2-1:25, and amino acid in a quantity such that the amino acid to (Al+Zr) weight ratio amounts to 2:1-1:20, preferably to 1:1-1:10.

Further particularly preferred solid antiperspirant activated salt compositions, for example according to U.S. Pat. No. 6,245,325 or U.S. Pat. No. 6,042,816, contain 48-78 wt. % (USP), preferably 66-75 wt. %, of an activated aluminum salt and 1-16 wt. %, preferably 4-13 wt. %, of molecularly bound water (water of hydration), furthermore water-soluble calcium salt in a quantity such that the Ca:Al weight ratio amounts to 1:1-1:28, preferably to 1:2-1:25, and glycine in a quantity such that the glycine to Al weight ratio amounts to 2:1-1:20, preferably to 1:1-1:10.

Further particularly preferred solid antiperspirant activated salt compositions, for example according to U.S. Pat. Nos. 6,245,325 or 6,042,816, contain 48-78 wt. % (USP), preferably 66-75 wt. %, of an activated aluminum salt and 1-16 wt. %, preferably 4-13 wt. %, of molecularly bound water, furthermore water-soluble calcium salt in a quantity such that the Ca:Al weight ratio amounts to 1:1-1:28, preferably to 1:2-1:25, and hydroxyalkanoic acid in a quantity such that the hydroxyalkanoic acid to Al weight ratio amounts to 2:1-1:20, preferably 1:1-1:10.

Water-soluble calcium salts which are preferred for stabilizing the antiperspirant salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Amino acids which are preferred for stabilizing the antiperspirant salts are selected from glycine, alanine, leucine, isoleucine, β-alanine, valine, cysteine, serine, tryptophan, phenylalanine, methionine, β-amino-n-butanoic acid and γ-amino-n-butanoic acid and the salts thereof, in each case in the d form, the l form and the dl form; glycine is particularly preferred.

Hydroxyalkanoic acids which are preferred for stabilizing the antiperspirant salts are selected from glycolic acid and lactic acid.

Further preferred antiperspirant active ingredients are activated aluminum salts, as are for example disclosed in U.S. Pat. No. 6,902,723, containing 5-78 wt. % (USP) of an activated antiperspirant aluminum salt, an amino acid or hydroxyalkanoic acid in a quantity such as to provide an (amino acid or hydroxyalkanoic acid) to Al weight ratio of 2:1-1:20 and preferably of 1:1 to 1:10, together with a water-soluble strontium salt in a quantity such as to provide a water-soluble strontium salt in a quantity such as to provide an Sr:Al weight ratio of 1:1-1:28 and preferably of 1:2-1:25.

Particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, furthermore water-soluble strontium salt in a quantity such that the Sr:Al weight ratio amounts to 1:1-1:28, preferably to 1:2-1:25, and amino acid in a quantity such that the amino acid to Al weight ratio amounts to 2:1-1:20, preferably to 1:1-1:10.

Further particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, furthermore water-soluble strontium salt in a quantity such that the Sr:Al weight ratio amounts to 1:1-1:28, preferably to 1:2-1:25, and glycine in a quantity such that the glycine to Al weight ratio amounts to 2:1-1:20, preferably to 1:1-1:10.

Further particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, furthermore water-soluble strontium salt in a quantity such that the Sr:Al weight ratio amounts to 1:1-1:28, preferably to 1:2-1:25, and hydroxyalkanoic acid in a quantity such that the hydroxyalkanoic acid to Al weight ratio amounts to 2:1-1:20, preferably to 1:1-1:10.

Further preferred activated aluminum salts are those of the general formula $Al_2(OH)_{6-a}X_a$, in which X is Cl, Br, I or $NO_3$ and "a" is a value from 0.3 to 5, preferably from 0.8 to 2.5 and particularly preferably 1 to 2, such that the molar ratio of Al:X amounts to 0.9:1 to 2.1:1, as are for example disclosed in U.S. Pat. No. 6,074,632. Some water of hydration is generally associatively bound with these salts, typically 1 to 6 mol of water per mol of salt. Aluminum chlorohydrate (i.e. X is Cl in the above-stated formula) is particularly preferred and specifically 5/6-basic aluminum chlorohydrate, in which "a" amounts to 1, such that the molar ratio of aluminum to chlorine amounts to 1.9:1 to 2.1:1.

Further preferred antiperspirant active ingredients are disclosed in U.S. Pat. No. 6,663,854 and US 20040009133.

The antiperspirant active ingredients are present in undissolved, suspended form.

Where the antiperspirant active ingredients are present as a suspension in a water-immiscible carrier, it is preferred for reasons of product stability for the active ingredient particles to have a number-average particle size of 0.1-200 μm, preferably of 1-50 μm, particularly preferably of 3-20 μm and extremely preferably of 5-10 μm. Preferred active ingredient particles have a volume-average particle size of 0.2-220 μm, preferably of 3-60 μm, particularly preferably of 4-25 μm, furthermore preferably of 5-20 μm and extremely preferably of 10-15.5 μm.

Preferred aluminum salts have a molar metal-to-chloride ratio of 1.9-2.1, or, for sesquichlorohydrates, of 1.5:1-1.8:1.

Compositions which are particularly preferred according to the invention are characterized in that the at least one antiperspirant active ingredient is present in a quantity of 5-40 wt. %, preferably of 10-35 wt. %, particularly preferably of 11-28 wt. % and extremely preferably of 12-20 wt. %, relative to the total weight of active substance excluding water of crystallization (USP) in the total composition excluding propellant.

In one particularly preferred embodiment, the composition contains an astringent aluminum salt, in particular aluminum chlorohydrate, particularly preferably aluminum chlorohydrate with an active substance content excluding water of crystallization (USP) of 72-88 wt. %, relative to the raw material in itself. Preferred non-activated aluminum chlorohydrates are for example distributed in pulverulent form as Micro Dry®, Micro Dry® Ultrafine or Micro Dry®-323 by Summit/Reheis, as Chlorhydrol® (powder) and in activated form as Reach® 101, Reach® 103, Reach® 501 by Reheis/Summit or AACH-7171 by Summit. An aluminum sesquichlorohydrate is offered for sale by Reheis under the name Reach® 301, which is also particularly preferred.

The compositions according to the invention, which are applied as a spray, are preferably formulated in accordance with the requirements of the desired spray application.

The compositions according to the invention assume suspension form, i.e. the antiperspirant active ingredient and optionally further insoluble components are suspended in a liquid carrier. Such a dispersed system should be shaken before application.

In a further preferred embodiment according to the invention, the compositions according to the invention are formulated as a suspension sprayable with a propellant.

Preferred compositions according to the invention may, for example, be packaged in pump or squeeze dispensers, in particular in multichamber pump or squeeze dispensers. Such dispensers use air, in particular ambient air, as propellant or deliver the composition according to the invention by pumps.

In a further preferred embodiment of the invention, the composition is applied by means of a compressed or liquefied propellant.

Unless otherwise stated, all quantities are stated relative to the weight of the composition excluding propellant.

Packaging in a multichamber dispenser offers particular technical advantages.

The multichamber dispenser may also be used such that one chamber is filled with the composition according to the invention, while another chamber contains the compressed propellant. One such multichamber dispenser is for example a "bag-in-can" package.

They two chambers may, however, also be connected to one another in such a manner that the composition according to the invention is divided into two sub-compositions which may simultaneously be discharged from the package, for example from separate orifices or from a single orifice.

Further compositions which are preferred according to the invention are characterized in that they are packaged with at least one propellant in a suitable pressure container.

Propellants (propellant gases) which are preferred according to the invention are selected from propane, propene, n-butane, iso-butane, iso-butene, n-pentane, pentene, iso-pentane, iso-pentene, methane, ethane, dimethyl ether, nitrogen, air, oxygen, laughing gas, dichlorofluoromethane, chlorodifluoromethane, chlorofluoromethane, 1,1,2,2-tetrachloro-1-fluoroethane, 1,1,1,2-tetrachloro-2-fluoroethane, 1,2,2-trichloro-1,1-difluoroethane, 1,1,2-trichloro-1,2-difluoroethane, 1,1,1-trichloro-2,2-difluoroethane, 2,2-dichloro-1,1,1-trifluoroethane, 1,2-dichloro-1,1,2-trifluoroethane, 2-chloro-1,1,1,2-tetrafluoroethane, 1-chloro-1,1,2,2-tetrafluoroethane, 1,1,2-trichloro-2-fluoroethane, 1,2-dichloro-1,2-difluoroethane, 1,2-dichloro-1,1-difluoroethane, 1-chloro-1,2,2-trifluoroethane, 2-chloro-1,1,1-trifluoroethane, 1-chloro-1,1,2-trifluoroethane, 1,2-dichloro-1-fluoroethane, 1,1-dichloro-1-fluoroethane, 2-chloro-1,1-difluoroethane, 1-chloro-1,1-difluoroethane, 1-chloro-2-fluoroethane, 1-chloro-1-fluoroethane, 2-chloro-1,1-difluoroethane, 1,1,1,3-tetrafluoroethane, heptafluoro-n-propane, perfluoroethane, monochlorodifluoromethane, 1,1-difluoroethane, and specifically both individually and in combination.

Propane, n-butane, iso-butane are particularly preferred and mixtures of these propellants are particularly preferred.

Hydrophilic propellant gases, such as for example carbon dioxide, may advantageously be used for the purposes of the present invention if a small proportion of hydrophilic gases is selected and a lipophilic propellant gas (for example propane/butane) is present in excess. Propane, n-butane, iso-butane and in particular mixtures of these propellant gases are particularly preferred.

The quantity of propellant preferably amounts to 20-95 wt. %, particularly preferably to 30-90 wt. % and extremely preferably to 60-86 wt. %, and furthermore extremely preferably to 75-78 wt. %, in each case relative to the total weight of the preparation consisting of the suspension according to the invention and the propellant.

Vessels of metal (aluminum, tin plate, tin), of protected or non-splintering plastics or of glass coated on the outside with plastics may be considered as the pressurized gas container, the selection of which is made on the basis not only of pressure resistance and breaking strength, corrosion resistance, ease of filling but also of aesthetic considerations, ease of handling, printability etc. Special internal protection lacquers ensure corrosion resistance relative to the suspension according to the invention. One internal protection lacquer which is preferred according to the invention is an epoxy-phenol lacquer, as is inter alia obtainable under the name Hoba 7407 P. The valves particularly preferably comprise an internally lacquered valve disc, the lacquer and valve material being mutually compatible. If aluminum valves are used, their valve discs may for example be coated on the inside with Micoflex lacquer. If tin plate valves are used according to the invention, their valve discs may for example be coated on the inside with PET (polyethylene terephthalate). Further compositions which are preferred according to the invention are characterized in that they contain at least one scent. Scents or perfume oils which may be used are individual fragrance compounds, for example synthetic products of the ester, ether, aldehyde, ketone, alcohol and hydrocarbon type. Phenolic fragrance compounds include for example carvacrol. Fragrance compounds of the ester type are for example benzyl acetate, methyl anthranilate, ortho-t-butylcyclohexyl acetate, p-tert.-butylcyclohexyl acetate, diethyl phthalate, 1,3-nonanediol diacetate, iso-nonyl acetate, iso-nonyl formate, phenylethyl phenyl acetate, phenoxyethyl isobutyrate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate, benzyl salicylate, ethyl salicylate, isoamyl salicylate, hexyl salicylate and 4-nonanolide. Ethers include, for example, benzyl ethyl ether, aldehydes include, for example, linear alkanals with 8 to 18 C atoms, citral, citronellal, citronellyloxyacetaldehyde, cyclamen aldehyde, hydroxycitronellal, lilial and bourgeonal, ketones include, for example, 6-acetyl-1,1,3,4,4,6- hexamethyltetrahydronaphthalene, para-t-amylcyclohexanone, 2-n-heptylcyclopentanone, β-methyl naphthyl ketone and the ionones α-isomethylionone and methyl cedryl ketone, alcohols include cinnamyl alcohol, anethole, citronellol, dimyrcetol, eugenol, geraniol, linalool, phenylethyl alcohol and terpineol, the hydrocarbons include 1,3,4,6,7,8-hexahydro-4,6,6,7,8,8-hexamethylcyclopenta-a-2-benzopyran, hydroxymethylisopropylcyclopentane, 3-a-methyldodecahydro-6,6,9a-trimethylnaphtho-2(2,1-b)furan, isobutylquinoline and the terpenes and balsams. Preferably, however, mixtures of various scents are used which together produce an attractive scent note.

Suitable perfume oils may also contain natural fragrance mixtures, as are obtainable from plant or animal sources, for example stone pine, citrus, jasmine, lily, rose or ylang-ylang oil. Relatively low volatility essential oils, which are generally used as aroma components, are also suitable as perfume oils, for example sage oil, chamomile oil, melissa oil, mint oil, cinnamon leaf oil, lime blossom oil, juniper berry oil, vetiver oil, olibanum oil, galbanum oil, laudanum oil, clove oil, iso-eugenol, thyme oil, bergamot oil, geranium oil and rose oil.

Compositions which are preferred according to the invention are characterized in that at least one scent is present in a total quantity of 0.1-10 wt. %, preferably of 0.2-7 wt. %, particularly preferably of 0.4-6 wt. %, extremely preferably of 1-5 wt. %, furthermore extremely preferably of 2-4 wt. %, in each case relative to the total weight of the composition excluding propellant.

Further compositions which are preferred according to the invention are characterized by a content of at least one "skin-cooling active ingredient". For the purposes of the present application, skin-cooling active ingredients are taken to mean active ingredients which, on application onto the skin, cause a pleasant sensation of coolness as a result of surface anesthesia and stimulation of the cold-sensitive nerves in migraine and the like, even if the treated areas of skin actually exhibit normal or elevated temperatures.

Preferred skin-cooling active ingredients are in particular menthol, isopulegol and menthol derivatives, for example menthyl lactate, menthyl pyrrolidone carboxylic acid, menthyl methyl ether, menthoxypropanediol, menthone glycerol acetal (9-methyl-6-(1-methylethyl)-1,4-dioxaspiro(4.5)decane-2-methanol), monomenthyl succinate and 2-hydroxymethyl-3,5,5-trimethylcyclohexanol. Particularly preferred skin-cooling active ingredients are menthol, isopulegol, menthyl lactate, menthoxypropanediol and menthyl pyrrolidone carboxylic acid.

Compositions which are preferred according to the invention contain at least one skin-cooling active ingredient in total quantities of 0.01-1.5 wt. %, preferably of 0.02-0.5 wt. % and particularly preferably of 0.05-0.2 wt. %, in each case relative to the total weight of the composition (excluding propellant).

Compositions which are preferred according to the invention are characterized in that at least one encapsulated active ingredient is present. The active ingredients, which may advantageously be encapsulated, are in particular scents, perfume oils and/or skin-cooling active ingredients, as well as other skin-conditioning active ingredients, such as vitamins, antioxidants etc.

Preferred encapsulating materials are water-soluble polymers such as starch, physically modified and/or chemically modified starches, cellulose derivatives, such as for example carboxymethylcellulose, methylcellulose, hydroxyethylcellulose or hydroxypropylmethylcellulose, carragheens, alginates, maltodextrins, dextrins, vegetable gums, pectins, xanthans, polyvinyl acetate and polyvinyl alcohol, polyvinylpyrrolidone, polyamides, polyesters and homo- and copolymers prepared from monomers, selected from acrylic acid, methacrylic acid, maleic acid, fumaric acid, itaconic acid together with the esters and the salts of these acids, together with any desired mixtures of these polymers.

Preferred encapsulating materials are chemically modified starches, in particular aluminum starch octenylsuccinate, for example the commercial product Dry Flo Plus from National Starch, or sodium starch octenylsuccinate, for example the commercial product Capsul from National Starch, moreover carboxymethylcellulose, carboxymethylcellulose, methylcellulose, hydroxyethylcellulose and hydroxypropylmethylcellulose, ethylcellulose, for example the commercial product Tylose H 10 from Clariant, furthermore carragheens, alginates and maltodextrins, and any desired mixtures of these polymers.

In a further embodiment which is preferred according to the invention, the compositions according to the invention contain 0 to at most 5 wt. % of ethanol, relative to the entire composition excluding propellant. For reasons of anticorrosion protection, ethanol contents of 0-3 wt. % are preferred, with ethanol contents of 0-1 wt. % being particularly preferred. The compositions according to the invention are substantially anhydrous, i.e. they contain 0 to at most 5 wt. %, preferably 0.5 to 4 wt. %, particularly preferably 1 to 3 wt. %, extremely preferably 1.5 to 2.5 wt. % of free water, in each case relative to the entire composition excluding propellant, free water contents of 1.6, 1.7, 1.8, 1.9, 2.0, 2.1, 2.2, 2.3 and 2.4 wt. % also possibly being preferred. The content of water of crystallization, water of hydration or similar molecularly bound water which is present in the components used, in particular in the antiperspirant active ingredients, does not constitute free water for the purposes of the present application.

The compositions according to the invention may furthermore contain additional deodorants. Antimicrobial, antibacterial or bacteriostatic substances, antioxidants or odor adsorbents (for example zinc ricinoleate) may be used as deodorants.

Suitable antimicrobial, antibacterial or bacteriostatic substances are in particular organohalogen compounds and halides, quaternary ammonium compounds, a series of plant extracts, colloidal, elemental silver, inorganic or organic silver salts, such as in particular silver citrate and silver dihydrogen citrate, and zinc compounds. Halogenated phenol derivatives are preferred, such as for example hexachlorophene or Irgasan DP 300 (triclosan, 2,4,4'-trichloro-2'-hydroxydiphenyl ether), 3,4,4'-trichlorocarbonilide, chlorhexidine (1,1'-hexamethylene bis-[5-(4-chlorophenyl)]-biguanide), chlorhexidine gluconate, benzalkonium halides and cetylpyridinium chloride. Sodium bicarbonate, sodium phenolsulfonate and zinc phenolsulfonate and for example components of lime blossom oil may furthermore be used. Antimicrobial substances which are relatively weakly active but have a specific action against the Gram-positive microorganisms responsible for breaking down perspiration may also be deodorant active ingredients. Benzyl alcohol may also be used as a deodorant active ingredient. Further antibacterially active deodorants are lantibiotics, glycoglycerolipids, sphingolipids (ceramides), sterols and other active ingredients which inhibit bacterial adhesion to the skin, for example glycosidases, lipases, proteases, carbohydrates, di- and oligosaccharide fatty acid esters and alkylated mono- and oligosaccharides. Preferred deodorant active ingredients are long-chain diols, for example 1,2-alkane-($C_5$-$C_{18}$)-diols, glycerol mono($C_8$-$C_{18}$)-fatty acid esters or, particularly preferably, glycerol mono-($C_6$-$C_{16}$)-alkyl ethers, in particular 2-ethylhexylglycerol ether, which have very good skin and mucous membrane compatibility and are active against corynebacteria, and furthermore phenoxyethanol, phenoxy-isopropanol (3-phenoxypropan-2-ol), anisyl alcohol, 2-methyl-5-phenylpentan-1-ol, 1,1-dimethyl-3-phenylpropan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2,2-dimethyl-3-phenylpropan-1-ol, 2,2-dimethyl-3-(3-methylphenyl)propan-1-ol, 2-ethyl-3-phenylpropan-1-ol, 2-ethyl-3-(3'-methylphenyl)-propan-1-ol, 3-(3'-chlorophenyl)-2-ethylpropan-1-ol, 3-(2'-chlorophenyl)-2-ethylpropan-1-ol, 3-(4'-chlorophenyl)-2-ethylpropan-1-ol, 3-(3',4'-dichlorophenyl)-2-ethylpropan-1-ol, 2-ethyl-3-(2'-methylphenyl)-propan-1-ol, 2-ethyl-3-(4'-methylphenyl)-propan-1-ol, 3-(3',4'-dimethylphenyl)-2-ethylpropan-1-ol, 2-ethyl-3-(4'-methoxyphenyl)propan-1-ol, 3-(3',4'-dimethoxyphenyl)-2-ethylpropan-1-ol, 2-allyl-3-phenylpropan-1-ol and 2-n-pentyl-3-phenylpropan-1-ol.

Complex-forming substances may also assist the deodorizing action by stably complexing heavy metal ions (for example iron or copper) which have an oxidative catalytic action. Suitable complexing agents are for example the salts of ethylenediaminetetraacetic acid or of nitrilotriacetic acid and the salts of 1-hydroxyethane-1,1-diphosphonic acid.

The compositions according to the invention may be packaged in conventional commercial aerosol cans. The cans may be made from tin plate or aluminum. The cans may furthermore be coated on the inside in order to keep the risk of corrosion as low as possible. The cans are equipped with a suitable spray head. Depending on the spray head, output rates, relative to completely full cans, of 0.1 g/s to 2.0 g/s are possible.

The present application also provides the use of an oil mixture prepared from 13-50 wt. % of triethyl citrate and 60-87 wt. % of at least one further cosmetic oil which is liquid under standard conditions and comprises 0 to less than 1 wt. % of cyclomethicone, for improving the reduction and/or regulation of perspiration and/or body odor by an antiperspirant composition which is formulated as a suspension which is sprayable with or without a propellant and contains at least one antiperspirant active ingredient and 0-5 wt. % of free water, relative to the weight of the composition excluding propellant. The above statements regarding the compositions according to the invention apply mutatis mutandis with regard to further preferred embodiments of this use according to the invention.

According to the invention "improving sweat reduction" should be taken to mean both a reduction in the quantity of sweat and accelerated release of the antiperspirant active ingredient from the composition according to the invention.

The present application also provides the non-therapeutic, cosmetic use of an antiperspirant composition according to the invention according to claim 1, 2, 3, 4, 5, 6, 7, 8, 9, 10, 11, 12 or 13 for reducing and/or regulating perspiration and/or body odor. The above statements regarding the compositions according to the invention apply mutatis mutandis with regard to further preferred embodiments of the uses according to the invention. The present application also provides a non-therapeutic, cosmetic method for reducing and/or regulating sweating and/or body odor, in which a composition according to the invention or preferred according to the invention according to any one of claim 1, 2, 3, 4, 5, 6, 7, 8, 9, 10, 11, 12 or 13 is applied in an effective quantity onto the skin, preferably onto the skin in the armpit area.

The above statements regarding the compositions according to the invention apply mutatis mutandis with regard to further preferred embodiments of the method according to the invention.

The following Examples are intended to clarify the invention but without limiting it thereto. All quantities are stated in wt. %.

Explanatory Notes:

The fill ratio denotes the weight ratio of antiperspirant composition (according to the invention or comparison composition) to propellant.

Measurement of Antiperspirant Active Ingredient Release

In order to ascertain whether the antiperspirant active ingredient is rapidly available, the time profile of the conductivity of the suspensions from a defined film was measured in a specific quantity of deionized water.

The value for conductivity reached at the end of the test is of the order of 80-160 microsiemens [µS] per centimeter for the compositions according to the invention. The prior art compositions exhibited a final conductivity of at most 10-50 microsiemens per centimeter.

Comparison compositions No. 1 to No. 5 and compositions Nos. 6-42 according to the invention were applied onto the skin in the armpit area.

A more rapid onset of antiperspirant action was observed for the compositions according to the invention.

The following tables provide a qualitative assessment of the tested compositions on a five point scale from "very good" to "poor". This assessment takes account not only of the final conductivity value achieved but also of the gradient of the change in conductivity over time at the start of the test. A steep gradient is interpreted to be synonymous with rapid release of the antiperspirant active ingredient.

The line * denotes the proportion by weight of triethyl citrate in the total quantity of oil c) plus d). Component e)=cyclomethicone was not present.

|  | No. 1 Comparison | No. 2 Comparison | No. 3 Comparison | No. 4 Comparison | No. 5 Comparison |
|---|---|---|---|---|---|
| Aluminium chlorohydrate | 28.57 | 32.11 | 14.29 | 28.57 | 32.11 |
| Disteardimonium Hectorite | 5.00 | 4.13 | 3.93 | 5.00 | 4.13 |
| Propylene carbonate | 1.50 | 1.50 | 0.71 | 1.64 | 1.00 |
| Fragrance | 7.14 | 4.59 | 6.50 | 6.50 | 5.00 |
| 2-Ethylhexyl palmitate | — | — | 74.57 | 58.29 | 57.76 |
| Cyclomethicone | 50.42 | 53.09 | — | — | — |
| Isopropyl myristate | 7.37 | 4.59 | — | — | — |

-continued

|  | No. 1 Comparison | No. 2 Comparison | No. 3 Comparison | No. 4 Comparison | No. 5 Comparison |
|---|---|---|---|---|---|
| Triethyl citrate | — | — | — | — | — |
| $C_{10}$-$C_{13}$ isoalkanes | — | — | — | — | — |
| Total | 100.00 | 100.00 | 100.00 | 100.00 | 100.00 |
| Fill ratio | 14:86 | 21.8:78.2 | 14:86 | 14:86 | 21.8:78.2 |
| Conductivity * | good | good | poor | poor | poor |

|  | No. 6 | No. 7 | No. 8 | No. 9 | No. 10 |
|---|---|---|---|---|---|
| Aluminium chlorohydrate | 28.57 | 32.11 | 14.29 | 28.57 | 32.11 |
| Disteardimonium Hectorite | 5.00 | 4.00 | 4.50 | 5.00 | 3.50 |
| Propylene carbonate | 1.30 | 1.50 | 0.50 | 1.80 | 1.30 |
| Fragrance | 7.00 | 5.00 | 7.00 | 7.00 | 4.59 |
| 2-Ethylhexyl palmitate | — | — | — | — | — |
| Cyclomethicone | — | — | — | — | — |
| Isopropyl myristate | 10.00 | 10.00 | 25 | 19.22 | 18.81 |
| Triethyl citrate | 12.13 | 12.0 | 24.06 | 19.2 | 19.50 |
| $C_{10}$-$C_{13}$ isoalkanes | 36.00 | 35.39 | 24.65 | 19.21 | 20.20 |
| Total | 100.00 | 100.00 | 100.00 | 100.00 | 100.00 |
| Fill ratio | 14:86 | 21.8:78.2 | 14:86 | 14:86 | 21.8:78.2 |
| Conductivity * | moderate 20.9 | moderate | moderate 33.9 | moderate | moderate 33.3 |

|  | No. 11 | No. 12 | No. 13 | No. 14 | No. 15 | No. 16 |
|---|---|---|---|---|---|---|
| Aluminium chlorohydrate | 14.29 | 28.57 | 32.11 | 14.29 | 28.57 | 32.11 |
| Disteardimonium Hectorite | 4.00 | 5.00 | 4.13 | 3.93 | 5.00 | 4.13 |
| Propylene carbonate | 0.71 | 1.50 | 1.50 | 0.50 | 1.50 | 1.40 |
| Fragrance | 7.14 | 7.10 | 4.50 | 7.14 | 7.10 | 4.50 |
| 2-Ethylhexyl palmitate | — | — | — | 19.12 | 15 | 15.00 |
| Isopropyl myristate | 19.12 | 15 | 15.00 | — | — | — |
| Triethyl citrate | 25.42 | 20 | 20 | 25.49 | 20 | 20.06 |
| $C_{10}$-$C_{13}$ isoalkanes | 29.32 | 22.83 | 22.76 | 29.53 | 22.83 | 22.8 |
| Total | 100.0 | 100.0 | 100.00 | 100.00 | 100.00 | 100.00 |
| Fill ratio | 14:86 | 14:86 | 21.8:78.2 | 14:86 | 14:86 | 21.8:78.2 |
| Conductivity * | moderate 34.3 | moderate 41.8 | moderate 34.6 | adequate 34.8 | adequate 34.6 | adequate |

| INCI | No. 17 | No. 18 | No. 19 |
|---|---|---|---|
| Aluminium chlorohydrate | 14.29 | 28.57 | 32.11 |
| Disteardimonium Hectorite | 4.00 | 5.00 | 4.00 |
| Propylene carbonate | 0.70 | 1.50 | 1.40 |
| Fragrance | 7.08 | 7.28 | 4.59 |
| Isopropyl myristate | 10 | 10.00 | 10.10 |
| Triethyl citrate | 12 | 12.00 | 12.0 |
| $C_{10}$-$C_{13}$ isoalkanes | 50.93 | 34.65 | 34.8 |

| INCI | No. 17 | No. 18 | No. 19 |
|---|---|---|---|
| PEG/PPG-22/24 Dimethicone (Mirasil DMCO) | 1 | 1 | 1 |
| Total | 100.00 | 100.00 | 100.00 |
| Fill ratio | 14:86 | 14:86 | 21.8:78.2 |
| Conductivity | good | good | good |
| * | | 16.5 | 21.2 |

| INCI | No. 20 | No. 21 | No. 22 |
|---|---|---|---|
| Aluminium chlorohydrate | 14.29 | 28.57 | 32.11 |
| Disteardimonium Hectorite | 4.00 | 5.00 | 4.00 |
| Propylene carbonate | 0.71 | 1.70 | 1.40 |
| Fragrance | 6.50 | 7.14 | 4.59 |
| Isopropyl myristate | 10 | 10.00 | 10.00 |
| Triethyl citrate | 12 | 12.00 | 12.1 |
| $C_{10}$-$C_{13}$ isoalkanes | 50.5 | 33.59 | 33.8 |
| PEG/PPG-22/24 Dimethicone (Mirasil DMCO) | 2 | 2 | 2 |
| Total | 100.00 | 100.00 | 100.00 |
| Fill ratio | 14:86 | 14:86 | 21.8:78.2 |
| Conductivity | good | good | good |
| * | | | |

| INCI | No. 23 | No. 24 | No. 25 | No. 26 | No. 27 |
|---|---|---|---|---|---|
| Aluminium chlorohydrate | 14.29 | 28.57 | 32.11 | 14.29 | 28.57 |
| Disteardimonium Hectorite | 3.93 | 5.00 | 4.13 | 3.93 | 5.00 |
| Propylene carbonate | 0.71 | 1.64 | 1.38 | 0.50 | 1.50 |
| Fragrance | 7.14 | 7.14 | 4.59 | 7.10 | 6.50 |
| Isopropyl myristate | 24.64 | 19.22 | 18.81 | 24.64 | 19.22 |
| Triethyl citrate | 24.64 | 19.22 | 19.50 | 24.64 | 20 |
| $C_{10}$-$C_{13}$ isoalkanes | 23.65 | 18.21 | 18.50 | 22.91 | 17.21 |
| PEG/PPG-22/24 Dimethicone (Mirasil DMCO) | 1 | 1 | 1 | 2 | 2 |
| PEG/PPG-10/2 Dimethicone Mirasil DMCP 93 | — | — | — | — | — |
| Total | 100.00 | 100.00 | 100.00 | 100.00 | 100.00 |
| Fill ratio | 14:86 | 14:86 | 21.8:78.2 | 14:86 | 14:86 |
| Conductivity | good | good | good | good | good |
| * | 33.8 | 33.9 | | 34.1 | 35.4 |

| INCI | No. 28 | No. 29 | No. 30 | No. 31 |
|---|---|---|---|---|
| Aluminium chlorohydrate | 32.11 | 14.29 | 28.57 | 32.11 |
| Disteardimonium Hectorite | 4.00 | 3.93 | 4.00 | 4.13 |
| Propylene carbonate | 1.38 | 0.50 | 1.64 | 1.30 |
| Fragrance | 4.50 | 7.15 | 7.14 | 5.00 |
| Isopropyl myristate | 19.02 | 10 | 10.00 | 10.00 |
| Triethyl citrate | 19.50 | 12.21 | 13.00 | 12.0 |
| $C_{10}$-$C_{13}$ isoalkanes | 17.50 | 50.93 | 34.65 | 34.46 |
| PEG/PPG-22/24 Dimethicone (Mirasil DMCO | 2 | — | — | — |
| PEG/PPG-10/2 Dimethicone Mirasil DMCP 93 | — | 1 | 1 | 1 |
| Total | 100.00 | 100.00 | 100.00 | 100.00 |
| Fill ratio | 21.8:78.2 | 14:86 | 14:86 | 21.8:78.2 |
| Conductivity | good | good | good | good |
| * | | | 16.7 | |

| INCI | No. 32 | No. 33 | No. 34 | No. 35 | No. 36 |
|---|---|---|---|---|---|
| Aluminium chlorohydrate | 14.29 | 28.57 | 32.11 | 14.29 | 28.57 |
| Disteardimonium Hectorite | 4.00 | 5.00 | 4.13 | 4.00 | 5.00 |
| Propylene carbonate | 0.71 | 1.50 | 1.40 | 0.71 | 1.60 |
| Fragrance | 6.50 | 7.14 | 4.60 | 7.00 | 7.14 |
| Isopropyl myristate | 10.57 | 10.00 | 10.00 | 24.71 | 19.22 |
| Triethyl citrate | 12 | 12.14 | 12.0 | 24.64 | 19.26 |
| $C_{10}$-$C_{13}$ isoalkanes | 49.93 | 33.65 | 33.76 | 23.65 | 18.21 |
| PEG/PPG-10/2 Dimethicone Mirasil DMCP 93) | 2 | 2 | 2 | 1 | 1 |
| Total | 100.00 | 100.00 | 100.00 | 100.00 | 100.00 |
| Fill ratio | 14:86 | 14:86 | 21.8:78.2 | 14:86 | 14:86 |
| Conductivity | good | good | good | moderate-good | moderate-good |
| * | 16.6 | | | | |

| INCI | No. 37 | No. 38 | No. 39 | No. 40 |
|---|---|---|---|---|
| Aluminium chlorohydrate | 32.11 | 14.29 | 28.57 | 32.11 |
| Disteardimonium Hectorite | 4.10 | 4.00 | 5.00 | 4.50 |
| Propylene carbonate | 1.40 | 0.50 | 1.00 | 1.40 |
| Fragrance | 4.50 | 7.00 | 8.00 | 4.50 |
| Isopropyl myristate | 18.81 | 24.64 | 19.22 | 18.50 |
| Triethyl citrate | 19.50 | 22.92 | 19 | 19.50 |
| $C_{10}$-$C_{13}$ isoalkanes | 18.58 | 24.65 | 17.21 | 17.50 |
| PEG/PPG-10/2 Dimethicone Mirasil DMCP 93) | 1 | 2 | 2 | 2 |
| Total | 100.00 | 100.00 | 100.00 | 100.00 |
| Fill ratio | 21.8:78.2 | 14:86 | 14:86 | 21.8:78.2 |
| Conductivity | moderate-good | good | good | good |

*

| INCI | No. 41 | No. 42 |
|---|---|---|
| Aluminium chlorohydrate | 32.11 | 32.11 |
| Disteardimonium Hectorite | 4.70 | 4.00 |
| Propylene carbonate | 1.38 | 1.38 |
| Fragrance | 4.00 | 4.13 |
| Isopropyl myristate | 10.00 | 10.00 |
| Triethyl citrate | 12.0 | 12.0 |
| $C_{10}$-$C_{13}$ isoalkanes | 33.62 | 34.19 |
| PEG/PPG-22/24 Dimethicone (Mirasil DMCO) | 1 | — |
| PEG/PPG-10/2 Dimethicone Mirasil DMCP 93) | — | 1 |
| Encapsulated perfume | 1.19 | 1.19 |
| Total | 100.00 | 100.00 |
| Fill ratio | 21.8:78.2 | 21.8:78.2 |
| Conductivity | good | good |

List of Raw Materials Used

| INCI name | Raw material name | Manufacturer/supplier |
|---|---|---|
| Disteardimonium Hectorite | Bentone Powder 38 V CG | Elementis Specialties |
| PEG/PPG-22/24 Dimethicone | Mirasil DMCO (72 wt. % PEG/PPG-22/24 Dimethicone active substance), linear polysiloxane-polyoxyalkylene block copolymer | Rhodia |
| PEG/PPG-10/2 Dimethicone | Mirasil DMCP 93 (93 wt. % PEG/PPG-10/2 Dimethicone active substance), linear polysiloxane-polyoxyalkylene block copolymer | Rhodia |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant composition for personal hygiene, formulated as a suspension which is sprayable with or without a propellant, comprising:
   a) at least one antiperspirant active ingredient,
   b) 0-5 wt. % of free water, relative to the weight of the composition excluding propellant,
   c) triethyl citrate,
   d) at least one further cosmetic oil which is liquid as carrier,
   e) 0 to less than 1 wt. % of cyclomethicone, relative to the weight of the composition excluding propellant,
   wherein the proportion by weight of triethyl citrate in the total quantity of oils c) plus d) plus e), relative to the entire composition excluding propellant, amounts to 13-50 wt. %, and release of said antiperspirant active from said antiperspirant composition is improved, as compared to the same antiperspirant composition not containing said 13-50 wt. percent triethyl citrate.

2. The composition according to claim 1, wherein the total quantity of triethyl citrate and at least one further cosmetic oil which is liquid d)+e) amounts to 30-95 wt. % relative to the entire composition excluding propellant.

3. The composition according to claim 1, wherein, in addition to triethyl citrate, at least one volatile non-silicone oil is present.

4. The composition according to claim 1, wherein the at least one carrier oil d) is liquid under standard conditions, and is a volatile non-silicone oil, and is selected from $C_8$-$C_{16}$ isoparaffins.

5. The composition according to claim 4, wherein the at least one carrier oil d) is selected from the group consisting of $C_{10}$-$C_{13}$ isoparaffin mixtures.

6. The composition according to claim 4, wherein the at least one $C_8$-$C_{16}$ isoparaffin is present in a total quantity of 25-50 wt. % relative to the entire composition excluding propellant.

7. The composition according to claim 4, further comprising, in addition to triethyl citrate and the at least one $C_8$-$C_{16}$ isoparaffin, at least one non-volatile cosmetic oil, selected from the group consisting of non-volatile silicone oils and non-volatile non-silicone oils.

8. The composition according to claim 3, wherein the at least one non-volatile non-silicone oil is selected from esters of linear or branched saturated or unsaturated fatty alcohols having 2-30 carbon atoms with linear or branched saturated or unsaturated fatty acids having 2-30 carbon atoms, which may be hydroxylated, and from the benzoic acid esters of linear or branched $C_8$-$_{22}$ alkanols.

9. The composition according to claim 8, wherein the at least one non-volatile non-silicone oil is selected from the group consisting of isopropyl palmitate, isopropyl myristate, isopropyl stearate, hexyldecyl stearate, hexyldecyl laurate, isononyl isononanoate, 2-ethylhexyl palmitate, 2-ethylhexyl stearate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-hexyl laurate, n-decyl oleate, oleyl oleate, oleyl erucate, erucyl oleate, $C_{12}$-$C_{15}$ alkyl lactate, di-$C_{12}$-$C_{13}$-alkyl malate, $C_{12}$-$C_{15}$ alkyl benzoate, benzoic acid isostearyl ester, ethylhexyl benzoate and benzoic acid octyldodecyl ester.

10. The composition according to claim 1, wherein component d) is at least one mixture of d)i) at least one volatile $C_8$-$C_{16}$ isoparaffin and d)ii) at least one ester of linear or branched saturated or unsaturated fatty alcohols having 2-30 carbon atoms with linear or branched saturated or unsaturated fatty acids having 2-30 carbon atoms, which may be hydroxylated, or is at least one mixture of d)i) of at least one volatile $C_8$-$C_{16}$ isoparaffin and d)ii) at least one benzoic acid ester of linear or branched $C_8$-$_{22}$ alkanols.

11. The composition according to claim 10, wherein d)1) is selected from the group consisting of $C_{10}$-$C_{13}$ isoparaffin mixtures, and wherein triethyl citrate/ester/$C_{10}$-$C_{13}$ isoparaffin are present in ratios by weight of triethyl citrate/ester/$C_{10}$-$_{13}$ isoparaffin of (1-1.3):(0.6-1):(1-3).

12. The composition according to claim 1, wherein at least one organosiloxane-oxyalkylene copolymer is present, which is selected from the group consisting of a linear polysiloxane-polyoxyethylene-polyoxypropylene block copolymer with the INCI name PEG/PPG-22/24 Dimethicone and a linear polysiloxane-polyoxyethylene-polyoxypropylene block copolymer with the INCI name PEG/PPG-10/2 Dimethicone, and mixtures thereof.

13. The composition according to claim 12, wherein the at least one organosiloxane-oxyalkylene copolymer is present in a total quantity of 0.01-5 wt. % relative to the total weight of the composition excluding propellant.

14. The composition according to claim 1, wherein the proportion by weight of the total quantity of triethyl citrate in the total oil content c) plus d) plus e) amounts to 15-40 wt. %.

15. The composition according to claim 1, wherein the oil mixture c) plus d) is selected from triethyl citrate/2-ethylhexyl palmitate/isodecane/isoundecane/ isododecane/isotridecane, triethyl citrate/hexyldecyl laurate/isodecane/ isoundecane/isododecane/isotridecane, triethyl citrate/2-ethylhexyl stearate/isodecane/isoundecane/isododecane/isotridecane, triethyl citrate/isopropyl myristate/isodecane/isoundecane/isododecane/isotridecane, triethyl citrate/isopropyl palmitate/isononane/isodecane/isoundecane/isododecane/isotridecane, triethyl citrate/2-ethylhexyl laurate/isodecane/isoundecane/isododecane/isotridecane, triethyl citrate/$C_{12}$-$C_{15}$ alkyl lactate/isodecane/isoundecane/isododecane/isotridecane, triethyl citrate/$C_{12}$-$C_{15}$ alkyl benzoate/isodecane/isoundecane/isododecane/isotridecane and triethyl citrate/di-$C_{12}$-$C_{13}$-alkyl malate/isodecane/isoundecane/isododecane/isotridecane.

16. A method for reducing and/or regulating sweating and/or body odor, comprising applying an effective quantity of the composition according to claim 1 onto the skin.

* * * * *